US007208472B2

(12) United States Patent
Zioncheck et al.

(10) Patent No.: US 7,208,472 B2
(45) Date of Patent: Apr. 24, 2007

(54) PHARMACEUTICAL COMPOSITIONS INCLUDING VARIANTS OF VASCULAR ENDOTHELIAL CELL GROWTH FACTOR HAVING ALTERED PHARMACOLOGICAL PROPERTIES

(75) Inventors: Thomas F. Zioncheck, Montara, CA (US); Geralyn G. DeGuzman, Daly City, CA (US); Rodney Gene Keck, Castro Valley, CA (US)

(73) Assignee: Genentech, Inc., South San Francisco, CA (US)

( * ) Notice: Subject to any disclaimer, the term of this patent is extended or adjusted under 35 U.S.C. 154(b) by 747 days.

(21) Appl. No.: 10/200,050

(22) Filed: Jul. 19, 2002

(65) Prior Publication Data

US 2003/0032145 A1 Feb. 13, 2003

Related U.S. Application Data

(63) Continuation of application No. 08/802,052, filed on Feb. 14, 1997, now Pat. No. 6,485,942.

(51) Int. Cl.
*C07K 14/475* (2006.01)
*A61K 38/18* (2006.01)

(52) U.S. Cl. ............... 514/12; 530/399; 424/198.1
(58) Field of Classification Search ............... None
See application file for complete search history.

(56) References Cited

U.S. PATENT DOCUMENTS

| 5,073,492 A | 12/1991 | Chen et al. |
| 5,219,739 A | 6/1993 | Tischer et al. |
| 5,332,671 A | 7/1994 | Ferrara et al. |
| 5,464,815 A | 11/1995 | Chamow et al. |
| 5,607,918 A | 3/1997 | Eriksson et al. |
| 6,020,473 A | 2/2000 | Keyt et al. |
| 6,057,428 A | 5/2000 | Keyt et al. |
| 6,100,071 A | 8/2000 | Davis-Smith et al. |
| 6,395,707 B1 | 5/2002 | Zioncheck et al. |

FOREIGN PATENT DOCUMENTS

| EP | 0 506 477 A1 | 9/1992 |
| WO | WO 90/13649 A1 | 11/1990 |
| WO | WO 91/02058 A1 | 2/1991 |
| WO | WO 95/07097 A1 | 3/1995 |
| WO | WO 96/06641 A1 | 3/1996 |
| WO | WO 98/10071 | 3/1998 |

OTHER PUBLICATIONS

Bowie et al., "Deciphering the Message in Protein Sequences: Tolerance to Amino Acid Substitutions," Science 247: 1306-1310, 1990.
Breier et al., "Expression of Vascular Endothelial Growth Factor During Embryonic Angiogenesis and Endothelial Cell Differentiation," Development, 114:521-532 (1992).
Ferrara et al., "Pituitary Follicular Cells Secrete a Novel Heparin-Binding Growth Factor Specific for Vascular Endothelial Cells," Biophys. Res. Comm., 161:851-858 (1989).
Ferrara, N., "Vascular Endothelial Growth Factor," Laboratory Investigation, 72(6):615-618 (1995).
Gengrinovitch et al., "Platelet Factor-4 Inhibits the Mitogenic Activity of $VEGF_{121}$ and $VEGF_{165}$ Using Several Concurrent Mechanisms" J. Biol Chem. 270(25):15059-15065, 1995.
Keyt et al. "The Carboxyl-Terminal Domain (111-165) of Vascular Endothelial Growth Factor is Critical for its Mitogenic Potency," J. Biol Chem 271(13):7788-7795, 1996.
Ngo et al., "Computational Complexity, Protein Structure Prediction, and the Levinthal Paradox," in *The Protein Folding Problem and Tertiary Structure*. Merz, K. Jr. and Le Grand, S. (eds). Birkhauser, Boston, pp. 492-495, 1994.
Robson et al. *Introduction to Proteins and Protein Engineering*. New York, Elsevier, p. 41, 1986.
Schultz et al., Principles of Protein Structure, Springer-Verlag: New York, pp. 14-16 (1979).
Walter et al., "The In Vivo Bioactivity of Vascular Endothelial Growth Factor/Vascular Permeability Factor is Independent of N-Linked Glycosidation," Laboratory Investigation, 74(2):546-556 (Feb. 1996).
Wells, "Additivity of Mutational Effects in Proteins," Biochemistry 29:8509-8517, (1990).
Houck et al., 1992, *The Journal of Biochemistry*, 267(36):26031-26037 "Dual Regulation of Vascular Endothelial Growth Factor Bioavailability by Genetic and Proteolytic Mechanisms".
Kato et al., 1994, *Hepatology*, 20(2):417-424 "Heparin-hepatocyte growth factor complex with low plasma clearance and retained hepatocyte proliferating activity".
Mühlhauser et al., 1995, *Circulation Research*, 77:1077-1086 "$VEGF_{165}$ Expressed by a Replication-Deficient Recombinant Adenovirus Vector-Induces Angiogenesis *In Vivo*".
Rao et al., 1983, *Blood*, 61(6):1208-1214 "Effect of heparin on the *in vivo* release and clearance of human platelet factor 4".

*Primary Examiner*—Christine J. Saoud
(74) *Attorney, Agent, or Firm*—Merchant & Gould P.C.

(57) ABSTRACT

Described herein are pharmaceutical compositions including vascular endothelial cell growth factor (VEGF) variants having modifications in the C-terminal heparin binding domain. The variants exhibit reduced clearance rates for systemic administration generally at lower doses compared with native VEGF thus providing variants having longer availability for therapeutic effect.

7 Claims, 15 Drawing Sheets

```
  1  CAGTGTGCTG GCGGCCCGGC GCGAGCCGGC CCGGCCCCGG TCGGGCCTCC
-26

GAAACC  ATG AAC TTT CTG CTG TCT TGG GTG CAT TGG AGC
             M   N   F   L   L   S   W   V   H   W   S
     -26                                 -20

90  CTC GCC TTG CTG CTC TAC CTC CAC CAT GCC AAG TGG TCC CAG
-15  L   A   L   L   L   Y   L   H   H   A   K   W   S   Q
                         -10

GCT|GCA CCC ATG GCA GAA GGA GGA GGG CAG AAT CAT CAC
     A  |A   P   M   A   E   G   G   G   Q   N   H   H
     -1  +1         +5                          +10

171  GAA GTG GTG AAG TTC ATG GAT GTC TAT CAG CGC AGC TAC TGC
 13  E   V   V   K   F   M   D   V   Y   Q   R   S   Y   C
             +15                 +20                 +25

CAT CCA ATC GAG ACC CTG GTG GAC ATC TTC CAG GAG TAC
     H   P   I   E   T   L   V   D   I   F   Q   E   Y
                     +30                 +35

252  CCT GAT GAG ATC GAG TAC ATC TTC AAG CCA TCC TGT GTG CCC
 40  P   D   E   I   E   Y   I   F   K   P   S   C   V   P
     +40                 +45                 +50

CTG ATG CGA TGC GGG GGC TGC TGC AAT GAC GAG GGC CTG
     L   M   R   C   G   G   C   C   N   D   E   G   L
     +55                 +60                 +65

333  GAG TGT GTG CCC ACT GAG GAG TCC AAC ATC ACC ATG CAG ATT
 67  E   C   V   P   T   E   E   S   N   I   T   M   Q   I
                 +70                 +75                 +80

ATG CGG ATC AAA CCT CAC CAA GGC CAG CAC ATA GGA GAG
     M   R   I   K   P   H   Q   G   Q   H   I   G   E
                 +85                 +90

414  ATG AGC TTC CTA CAG CAC AAC AAA TGT GAA TGC AGA CCA AAG
 94  M   S   F   L   Q   H   N   K   C   E   C   R   P   K
         +95                 +100                +105

AAA GAT AGA GCA AGA CAA GAA AAT CCC TGT GGG CCT TGC
     K   D   R   A   R   Q   E   N   P   C   G   P   C
             +110                +115                +120

495  TCA GAG CGG AGA AAG CAT TTG TTT GTA CAA GAT CCG CAG ACG
121  S   E   R   R   K   H   L   F   V   Q   D   P   Q   T
                     +125                +130

TGT AAA TGT TCC TGC AAA AAC ACA GAC TCG CGT TGC AAG
     C   K   C   S   C   K   N   T   D   S   R   C   K
     +135                +140                +145
```

FIG._1A

```
576  GCG AGG CAG CTT GAG TTA AAC GAA CGT ACT TGC AGA TGT GAC
148   A   R   Q   L   E   L   N   E   R   T   C   R   C   D
             +150            +155                +160

AAG CCG AGG CGG TGA GCCGGGCA GGAGGAAGGA GCCTCCCTCA
      K   P   R   R   O
                 +165

661  GGGTTTCGGG AACCAGATCT CTCACCAGGA AAGACTGATA CAGAACGATC

GATACAGAAA CCACGCTGCC GCCACCACAC CATCACCATC GACAGAACAG

761  TCCTTAATCC AGAAACCTGA AATGAAGGAA GAGGAGACTC TGCGCAGAGC

ACTTTGGGTC CGGAGGGCGA GACTCCGGCG GAAGCATTCC CGGGCGGGTG

861  ACCCAGCACG GTCCCTCTTG GAATTGGATT CGCCATTTTA TTTTTCTTGC

TGCTAAATCA CCGAGCCCGG AAGATTAGAG AGTTTTATTT CTGGGATTCC

961  TGTAGACACA CCGCGGCCGC CAGCACACTG
```

FIG._1B

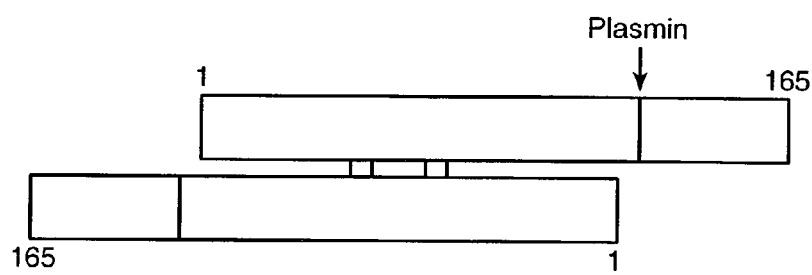
VEGF Structure
1
APMAEGGGGQNHHEVVKFMDVYQRS
YCHPIETLVDIFQEYPDEIEYIFKPSCVPLMRCGGCCNDEGL
ECVPTEESNITMQIMRIKPHQGQHIGEMSFLQHNKCECRPKKDRARQENPCGPCSERRKHLFVQ
CHO　　　　　　　　　　　　　　　　　DPQTCKCSCKNTDSRCKA
　　　　　　　　　　　　　　　　　　　RQLELNERTCRCDKPRR
　　　　　　　　　　　　　　　　　　　　　　　　　　　165
FIG._2

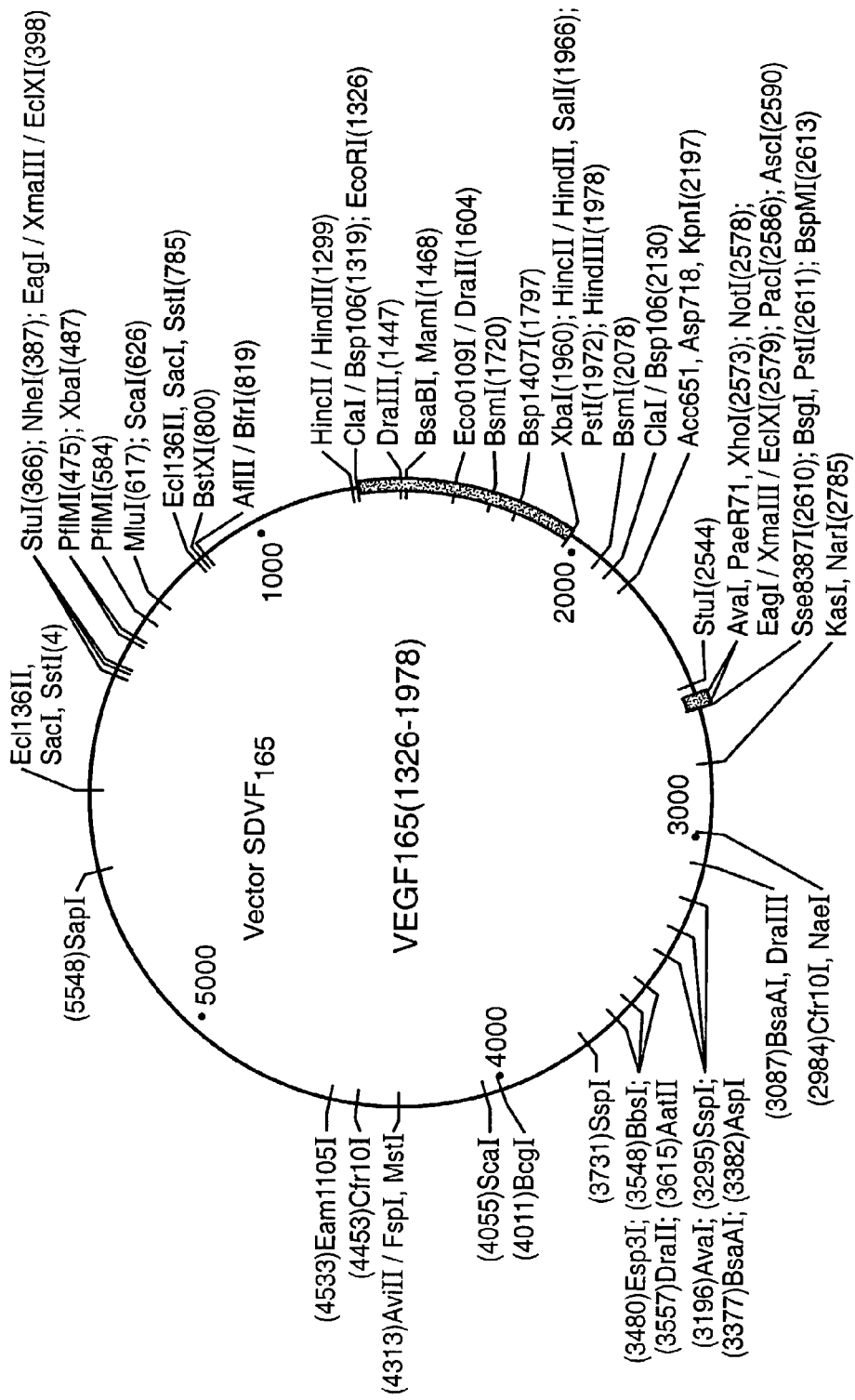
FIG._3

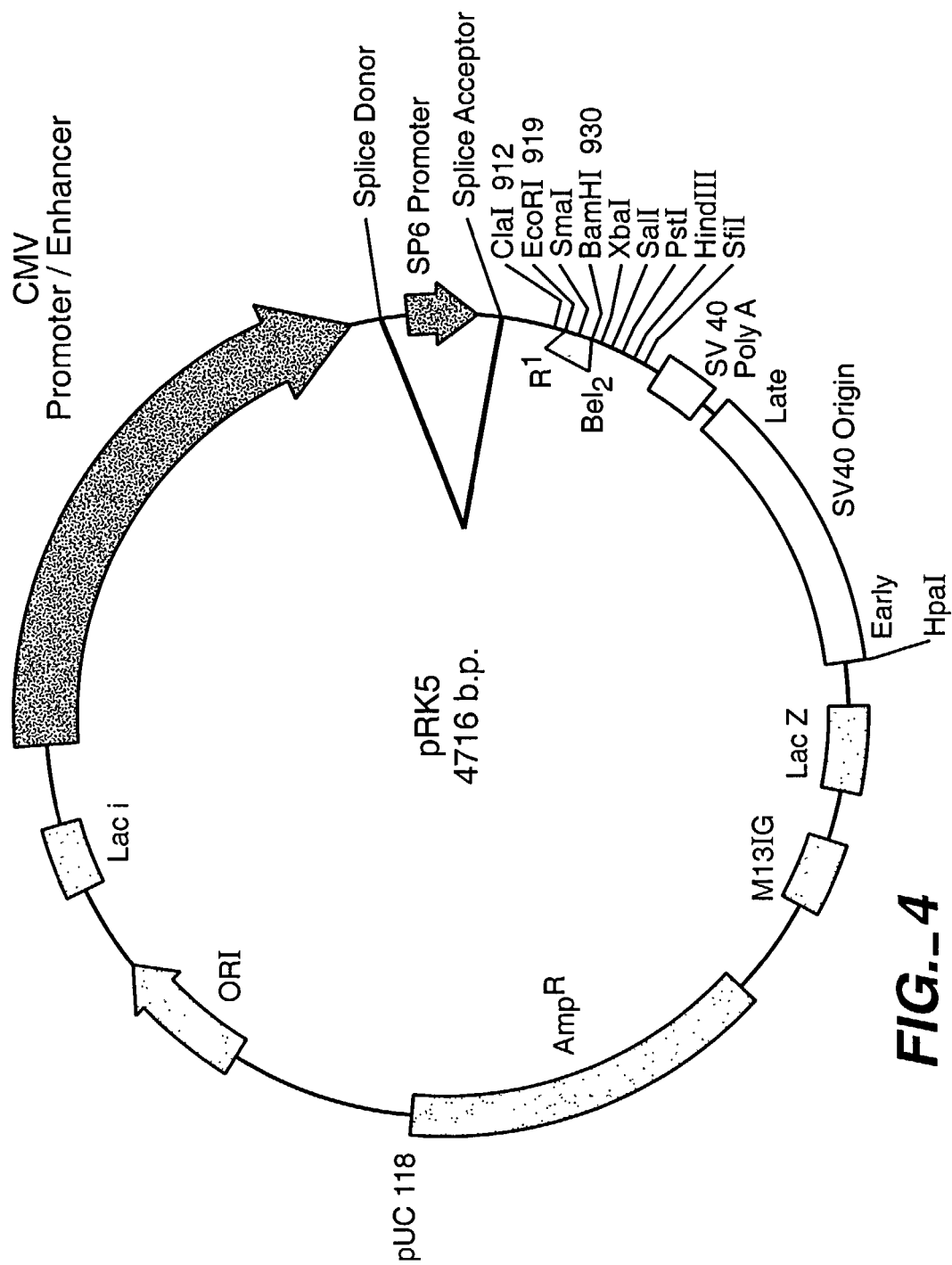
FIG._4

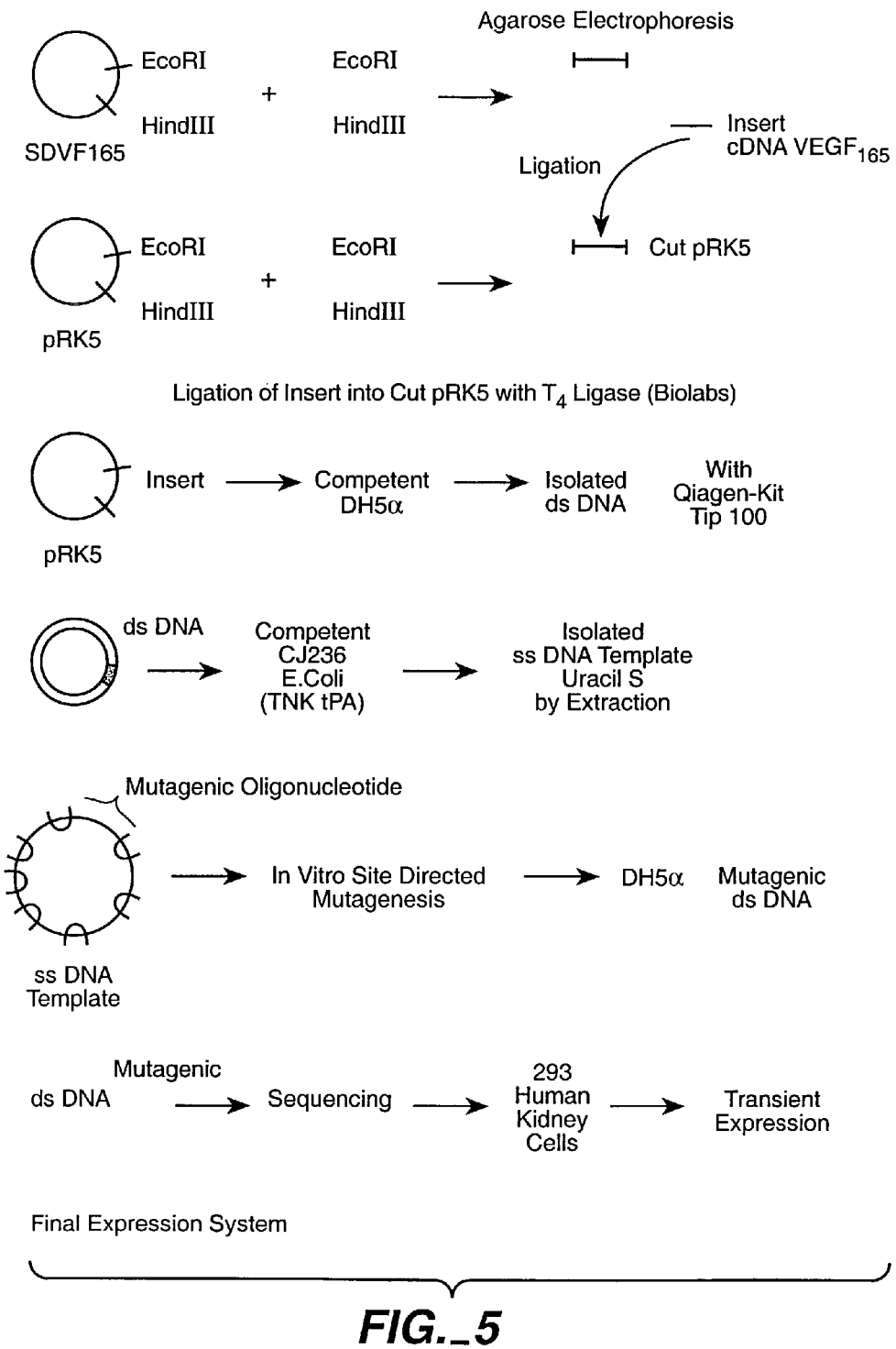
FIG._5

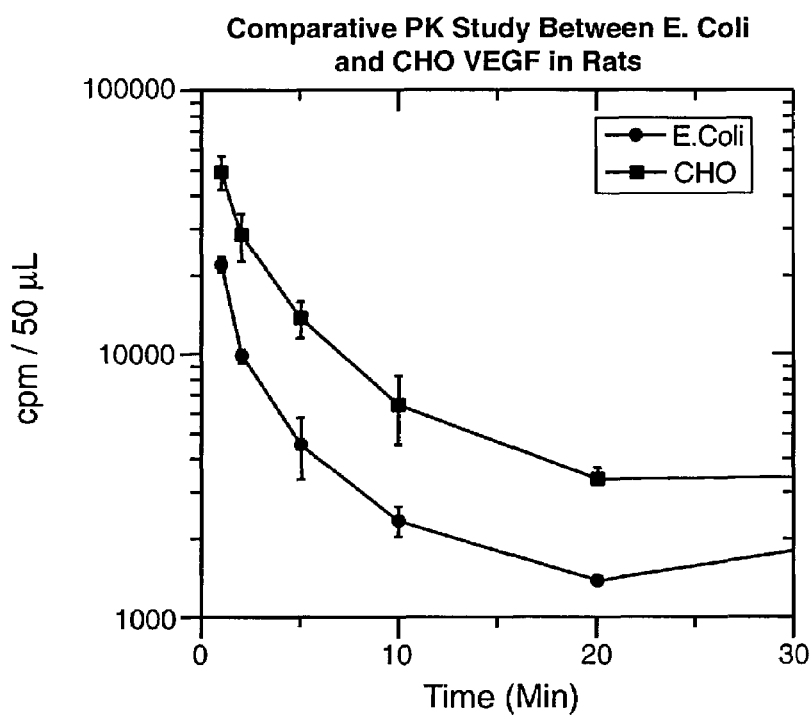
FIG._6
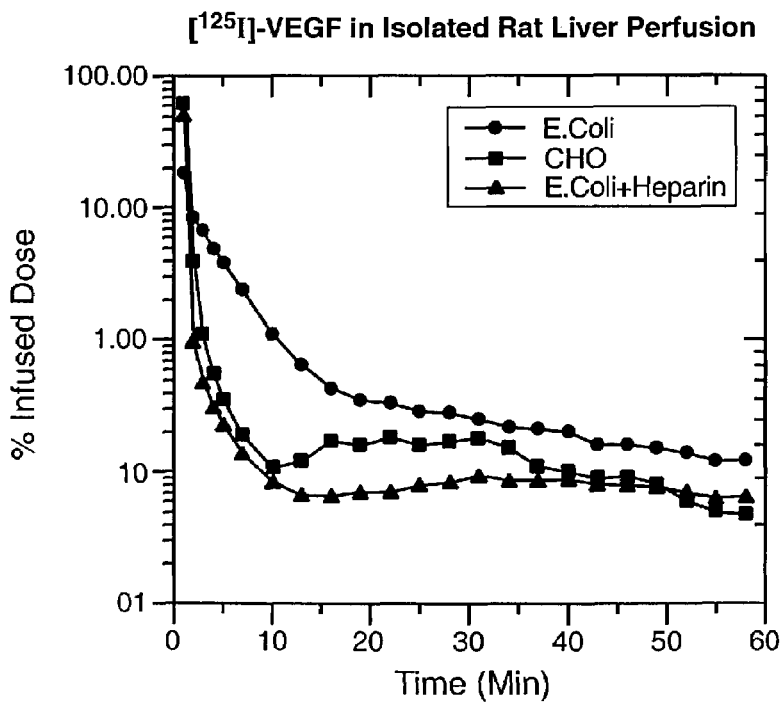
FIG._8

| ID | $^{125}$I-E.Coli | $^{125}$-CHO |
|---|---|---|
| CL (mL / min / kg) | 8.2±1.26 | 6.4±0.5 |
| Vdss (mL / kg) | 3419±352 | 2147±394 |
| t 1/2 (å) (min) 1/2 (ß) 1/2 (∂) | 0.99±1.54  297±4.3 | 2.2±0.4  257±53 |
| ID | $^{125}$I-E.Coli | $^{125}$I-CHO | $^{125}$I-E.Coli+Hep |
|---|---|---|---|
| CL (mL / min / kg) | 11.5 | 4.0 | 3.6 |
| Vdss (mL) | 1358.6 | 1263.9 | 1301.7 |
| t 1/2 (a) (min) | 2.3 | 5.0 | 3.3 |
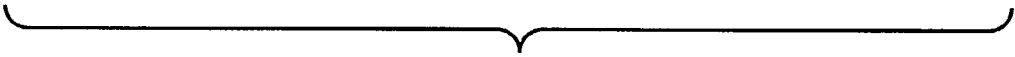
*FIG._7*

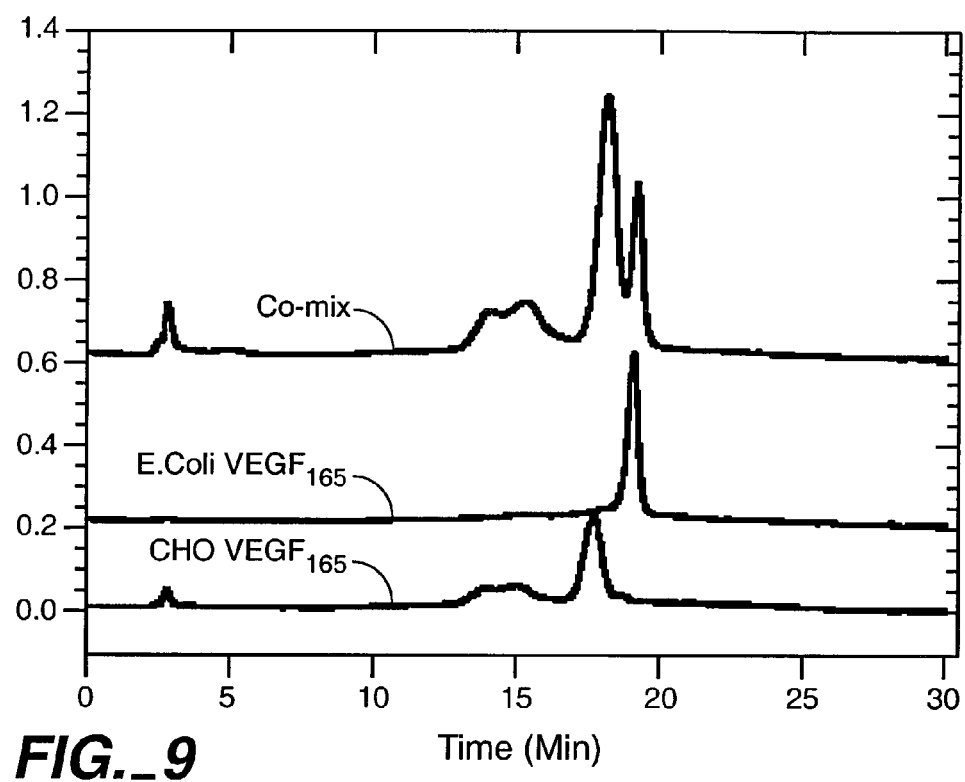
FIG._9
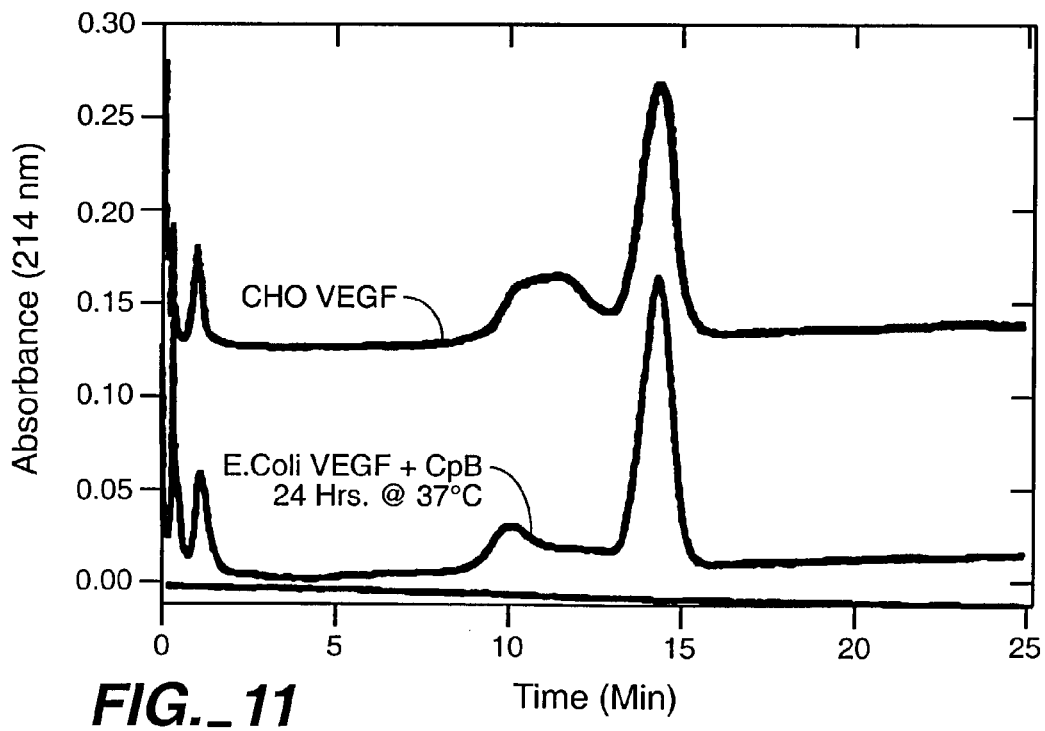
FIG._11

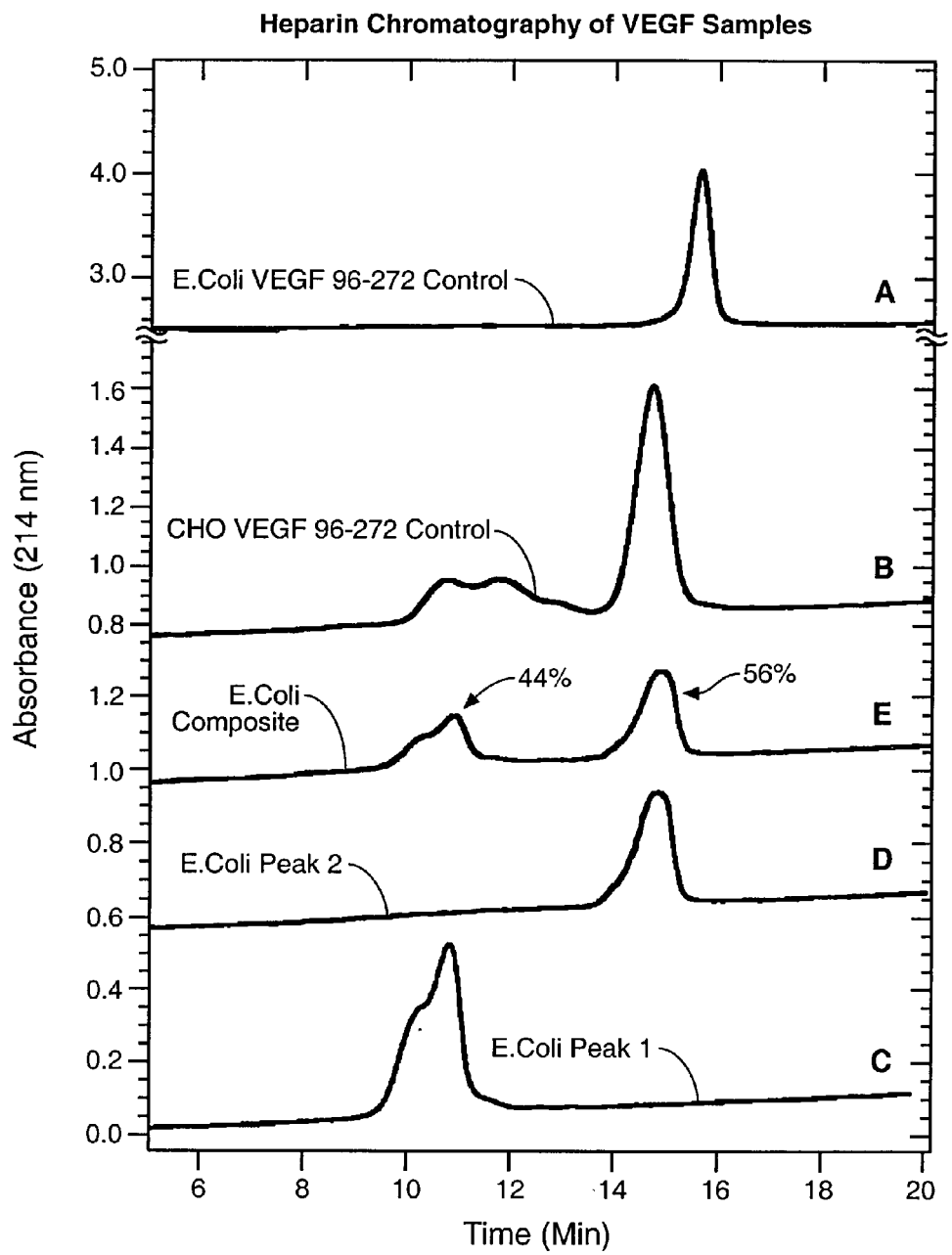
FIG._10

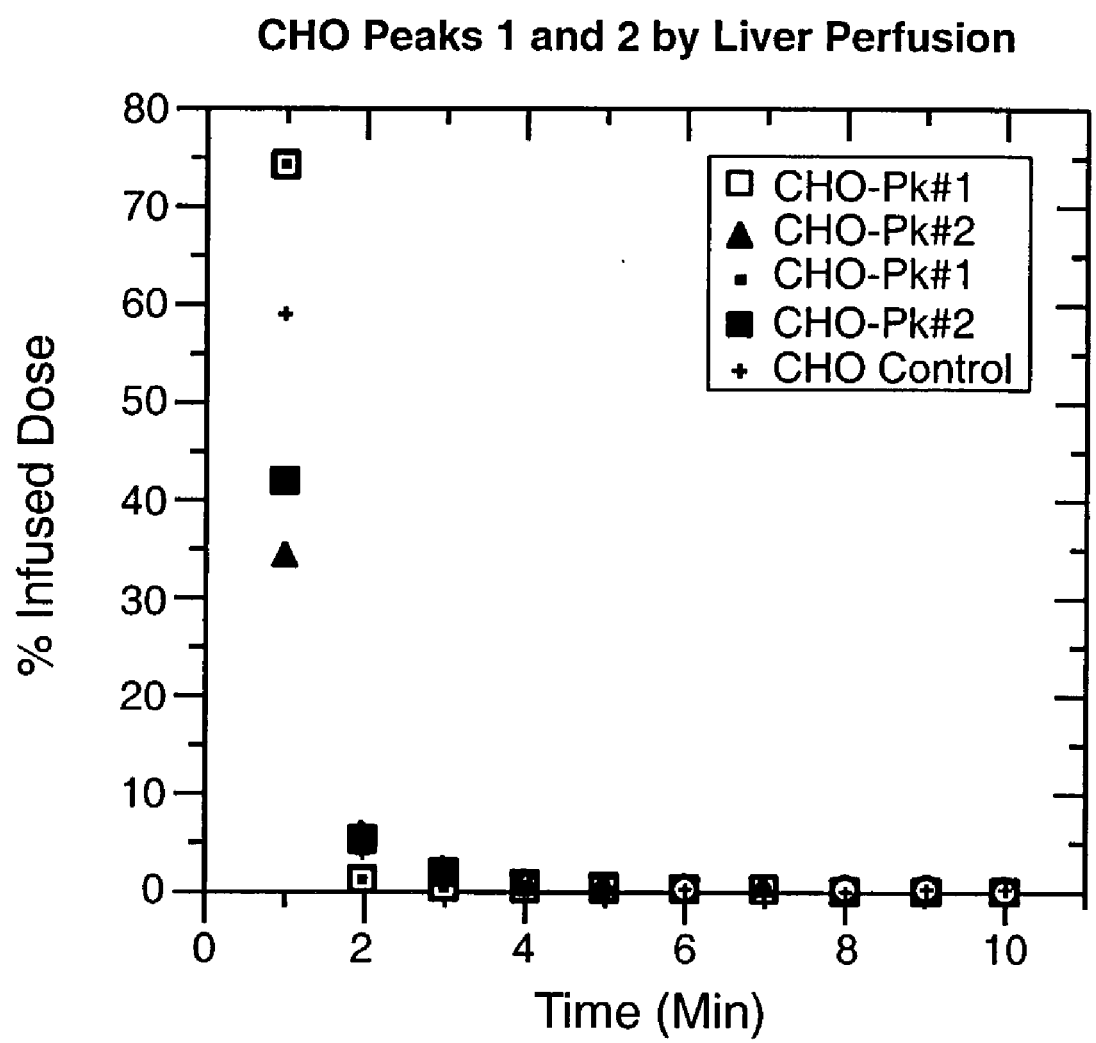
FIG._12

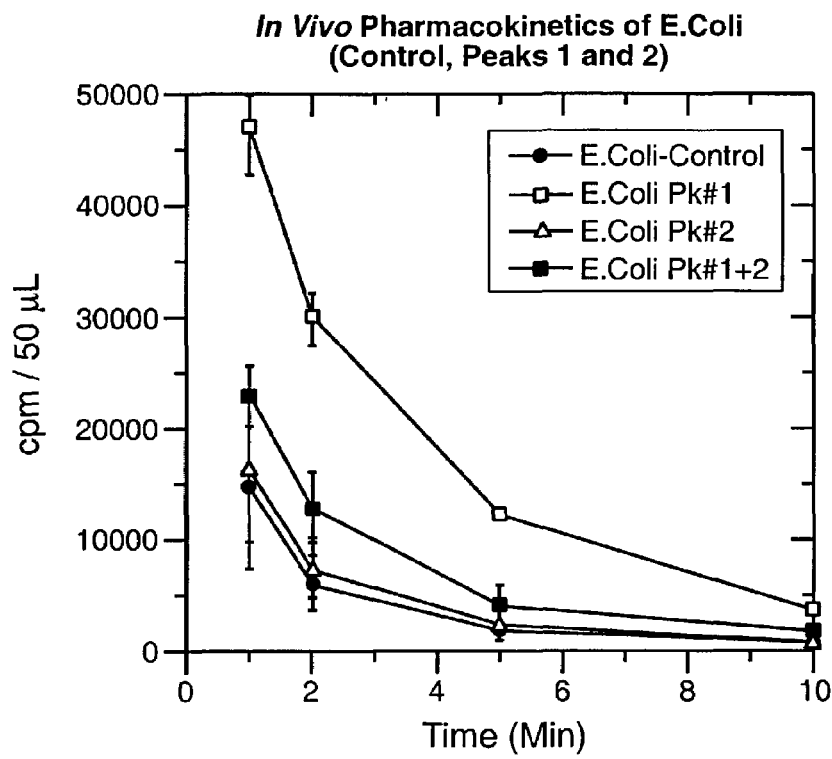
FIG._13
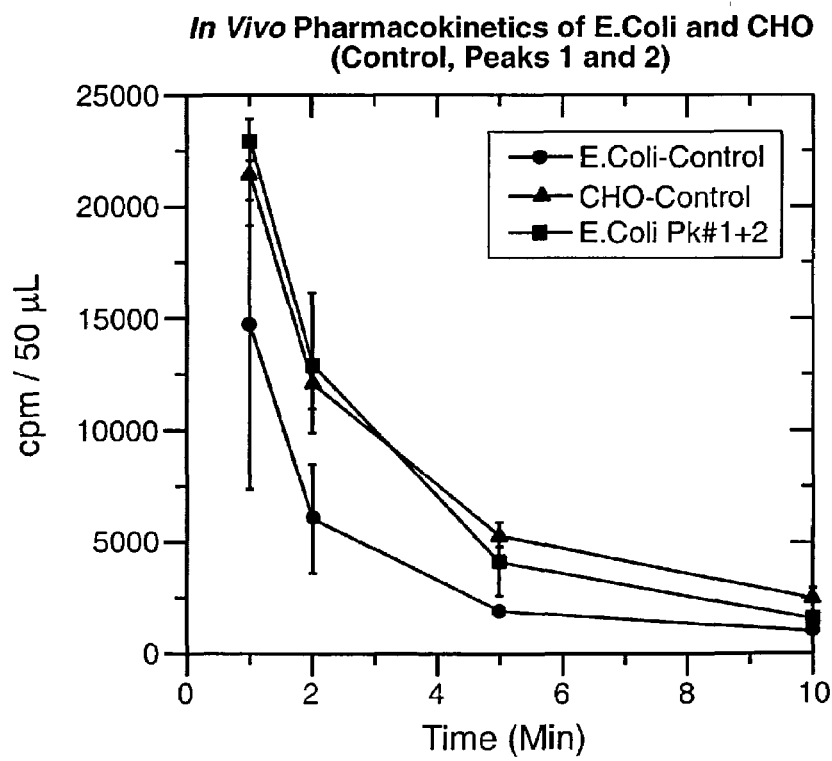
FIG._14

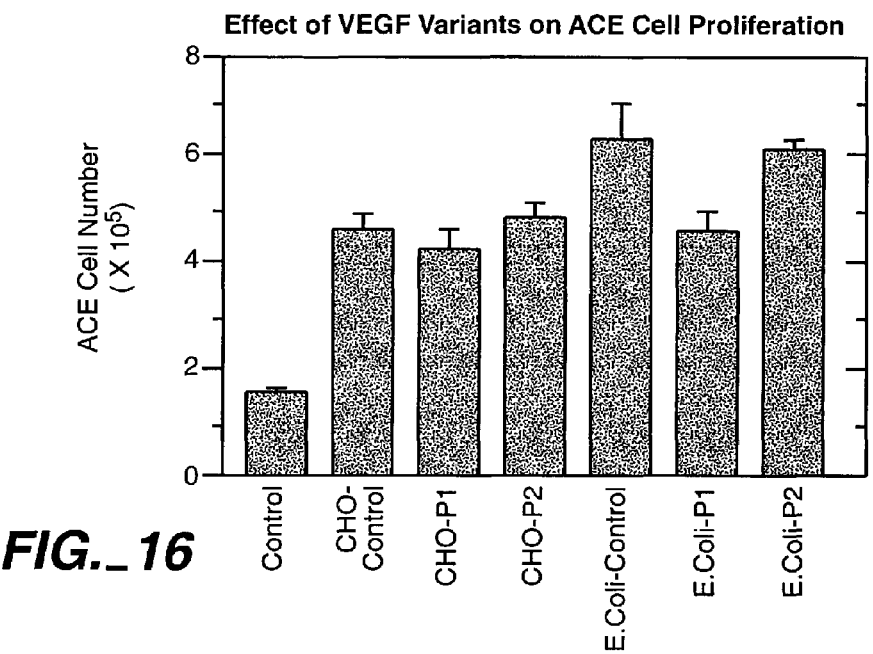
FIG._16
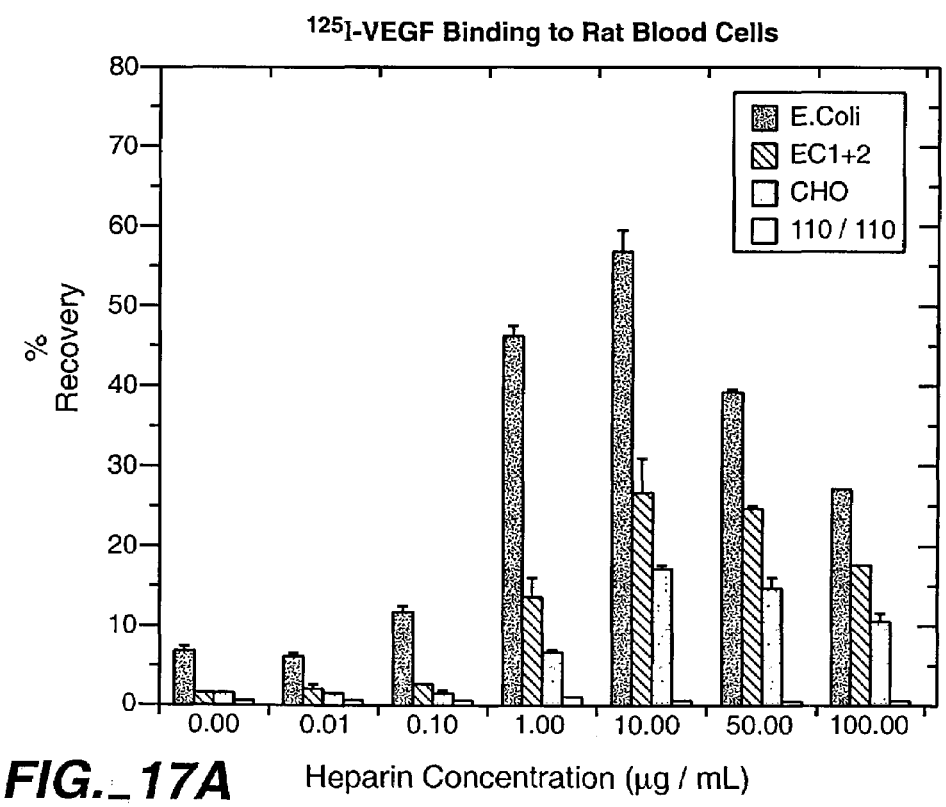
FIG._17A

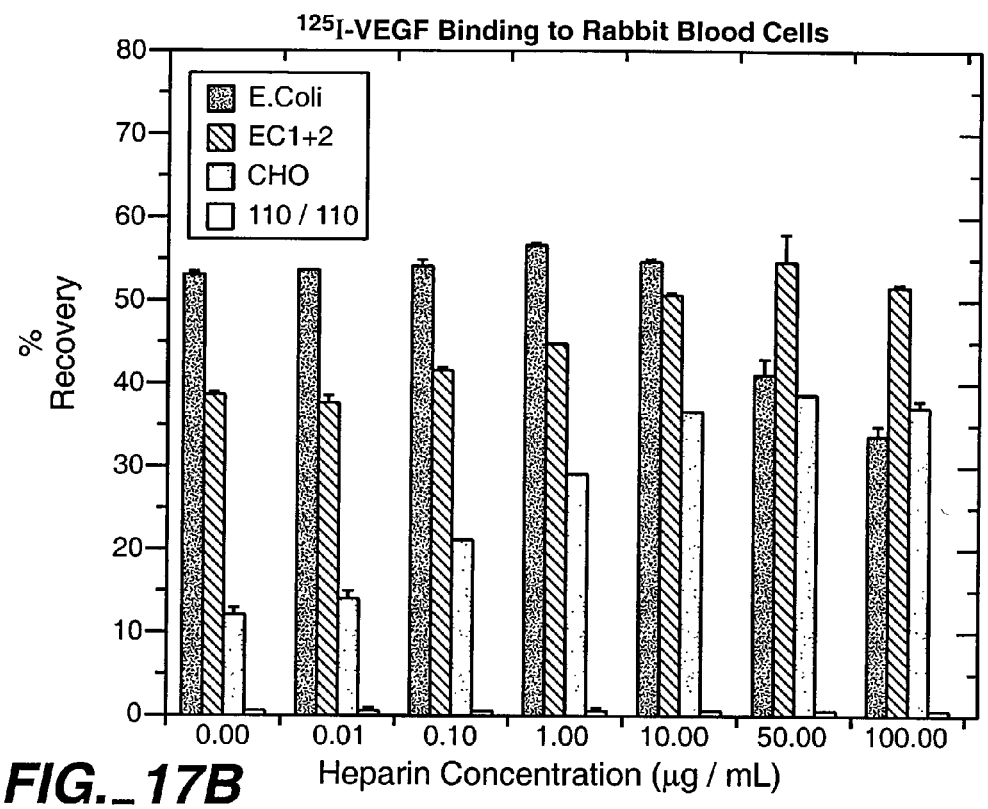
FIG.—17B
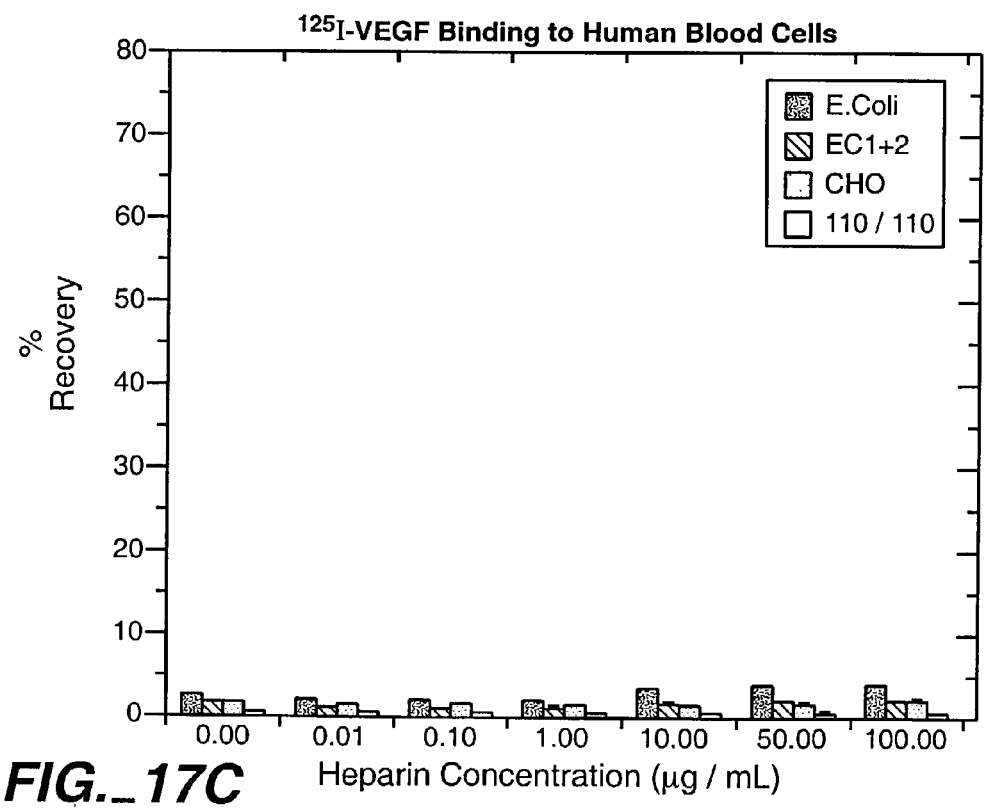
FIG.—17C

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 990 base pairs
      (B) TYPE: nucleic acid
      (C) STRANDEDNESS: unknown
      (D) TOPOLOGY: unknown (ii) MOLECULE TYPE: DNA (ix) FEATURE:
      (A) NAME/KEY: CDS
      (B) LOCATION: 57..630

(ix) FEATURE:
      (A) NAME/KEY: mat_peptide
      (B) LOCATION: 135..630

(xi) SEQUENCE DESCRIPTION: SEQ ID NO: 1:

```
CAGTGTGCTG GCGGCCCGGC GCGAGCCGGC CCGGCCCCGG TCGGGCCTCC GAAACC          56

ATG AAC TTT CTG CTG TCT TGG GTG CAT TGG AGC CTC GCC TTG CTG CTC      104
Met Asn Phe Leu Leu Ser Trp Val His Trp Ser Leu Ala Leu Leu Leu
-26 -25                 -20                 -15

TAC CTC CAC CAT GCC AAG TGG TCC CAG GCT GCA CCC ATG GCA GAA GGA      152
Tyr Leu His His Ala Lys Trp Ser Gln Ala Ala Pro Met Ala Glu Gly
-10                  -5                  1                5

GGA GGG CAG AAT CAT CAC GAA GTG GTG AAG TTC ATG GAT GTC TAT CAG      200
Gly Gly Gln Asn His His Glu Val Val Lys Phe Met Asp Val Tyr Gln
            10                  15                  20

CGC AGC TAC TGC CAT CCA ATC GAG ACC CTG GTG GAC ATC TTC CAG GAG      248
Arg Ser Tyr Cys His Pro Ile Glu Thr Leu Val Asp Ile Phe Gln Glu
        25                  30                  35

TAC CCT GAT GAG ATC GAG TAC ATC TTC AAG CCA TCC TGT GTG CCC CTG      296
Tyr Pro Asp Glu Ile Glu Tyr Ile Phe Lys Pro Ser Cys Val Pro Leu
            40                  45                  50

ATG CGA TGC GGG GGC TGC TGC AAT GAC GAG GGC CTG GAG TGT GTG CCC      344
Met Arg Cys Gly Gly Cys Cys Asn Asp Glu Gly Leu Glu Cys Val Pro
55                  60                  65                  70

ACT GAG GAG TCC AAC ATC ACC ATG CAG ATT ATG CGG ATC AAA CCT CAC      392
Thr Glu Glu Ser Asn Ile Thr Met Gln Ile Met Arg Ile Lys Pro His
                75                  80                  85

CAA GGC CAG CAC ATA GGA GAG ATG AGC TTC CTA CAG CAC AAC AAA TGT      440
Gln Gly Gln His Ile Gly Glu Met Ser Phe Leu Gln His Asn Lys Cys
            90                  95                  100

GAA TGC AGA CCA AAG AAA GAT AGA GCA AGA CAA GAA AAT CCC TGT GGG      488
```

```
        Glu Cys Arg Pro Lys Lys Asp Arg Ala Arg Gln Glu Asn Pro Cys Gly
                105                 110                 115

CCT TGC TCA GAG CGG AGA AAG CAT TTG TTT GTA CAA GAT CCG CAG ACG            536
Pro Cys Ser Glu Arg Arg Lys His Leu Phe Val Gln Asp Pro Gln Thr
    120                 125                 130

TGT AAA TGT TCC TGC AAA AAC ACA GAC TCG CGT TGC AAG GCG AGG CAG            584
Cys Lys Cys Ser Cys Lys Asn Thr Asp Ser Arg Cys Lys Ala Arg Gln
135                 140                 145                 150

CTT GAG TTA AAC GAA CGT ACT TGC AGA TGT GAC AAG CCG AGG CGG T              630
Leu Glu Leu Asn Glu Arg Thr Cys Arg Cys Asp Lys Pro Arg Arg
                155                 160                 165

GAGCCGGGCA GGAGGAAGGA GCCTCCCTCA GGGTTTCGGG AACCAGATCT CTCACCAGGA          690

AAGACTGATA CAGAACGATC GATACAGAAA CCACGCTGCC GCCACCACAC CATCACCATC          750

GACAGAACAG TCCTTAATCC AGAAACCTGA ATGAAGGAA GAGGAGACTC TGCGCAGAGC           810

ACTTTGGGTC CGGAGGGCGA GACTCCGGCG AAGCATTCC CGGGCGGGTG ACCCAGCACG           870

GTCCCTCTTG GAATTGGATT CGCCATTTTA TTTTTCTTGC TGCTAAATCA CCGAGCCCGG          930

AAGATTAGAG AGTTTTATTT CTGGGATTCC TGTAGACACA CCGCGGCCGC CAGCACACTG          990

(2) INFORMATION FOR SEQ ID NO: 2:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 2:

Met Asn Phe Leu Leu Ser Trp Val His Trp Ser Leu Ala Leu Leu Leu
-26 -25                 -20                 -15

Tyr Leu His His Ala Lys Trp Ser Gln Ala Ala Pro Met Ala Glu Gly
-10                 -5                  1                   5

Gly Gly Gln Asn His His Glu Val Val Lys Phe Met Asp Val Tyr Gln
                10                  15                  20

Arg Ser Tyr Cys His Pro Ile Glu Thr Leu Val Asp Ile Phe Gln Glu
                25                  30                  35

Tyr Pro Asp Glu Ile Glu Tyr Ile Phe Lys Pro Ser Cys Val Pro Leu
                40                  45                  50

Met Arg Cys Gly Gly Cys Cys Asn Asp Glu Gly Leu Glu Cys Val Pro
55                  60                  65                  70

Thr Glu Glu Ser Asn Ile Thr Met Gln Ile Met Arg Ile Lys Pro His
                75                  80                  85

Gln Gly Gln His Ile Gly Glu Met Ser Phe Leu Gln His Asn Lys Cys
                90                  95                  100

Glu Cys Arg Pro Lys Lys Asp Arg Ala Arg Gln Glu Asn Pro Cys Gly
                105                 110                 115

Pro Cys Ser Glu Arg Arg Lys His Leu Phe Val Gln Asp Pro Gln Thr
    120                 125                 130

Cys Lys Cys Ser Cys Lys Asn Thr Asp Ser Arg Cys Lys Ala Arg Gln
135                 140                 145                 150

Leu Glu Leu Asn Glu Arg Thr Cys Arg Cys Asp Lys Pro Arg Arg
                155                 160                 165

(2) INFORMATION FOR SEQ ID NO: 3:

(i) SEQUENCE CHARACTERISTICS:
```

(A) LENGTH: 165 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 3:

```
Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
        50                  55                  60

Gly Leu Glu Cys Val Pro Thr Glu Glu Ser Asn Ile Thr Met Gln Ile
65                      70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
            115                 120                 125

Val Gln Asp Pro Gln Thr Cys Lys Cys Ser Cys Lys Asn Thr Asp Ser
        130                 135                 140

Arg Cys Lys Ala Arg Gln Leu Glu Leu Asn Glu Arg Thr Cys Arg Cys
145                 150                 155                 160

Asp Lys Pro Arg Arg
                165
```

PHARMACEUTICAL COMPOSITIONS INCLUDING VARIANTS OF VASCULAR ENDOTHELIAL CELL GROWTH FACTOR HAVING ALTERED PHARMACOLOGICAL PROPERTIES

CROSS-REFERENCE TO RELATED APPLICATIONS

This is a continuation application of U.S. Ser. No. 08/802,052, filed Feb. 14, 1997, now U.S. Pat. No. 6,485,942.

This application contains subject matter related to the following patent applications: U.S. Ser. No. 08/691,794 filed 2 Aug. 1996, now U.S. Pat. No. 6,057,428; U.S. Ser. No. 08/567,200 filed 5 Dec. 1995, now U.S. Pat. No. 6,020,473; U.S. Ser. No. 60/002,827 filed 25 Aug. 1995; U.S. Ser. No. 07/389,722 filed 4 Aug. 1989 now U.S. Pat. No. 5,332,671; U.S. Ser. No. 07/369,424 filed 21 Jun. 1989, now abandoned; U.S. Ser. No. 07/351,117 filed 12 May 1989, now abandoned; U.S. Ser. No. 08/734,443 filed 17 Oct. 1996; and U.S. Ser. No. 08/643,839 filed 7 May 1996, now U.S. Pat. No. 6,100,071.

FIELD OF THE INVENTION

The present invention is directed to particular variants of vascular endothelial cell growth factor (hereinafter sometimes refers to as VEGF), to methods for preparing such variants, and to methods and compositions and assays utilizing such variants for producing pharmaceutically active materials having therapeutic properties not differing at least substantially in kind from the parent compound, VEGF, but having pharmacological properties that differ from the parent compound, VEGF. In particular, the assays using such variants can be employed to discover new materials having agonistic or antagonistic properties to VEGF.

The variants hereof have a demonstrated slower clearance rate compared with native material such that they are useful and perhaps safer alternatives for systemic administration as lower doses are available because of such reduced clearance rates; hence, these variants provide longer availability for therapeutic effect.

BACKGROUND OF THE INVENTION

VEGF is a naturally occurring compound that is produced in follicular or folliculo-stellate cells (FC), a morphologically well characterized population of granular cells. The FC are stellate cells that send cytoplasmic processes between secretory cells.

Several years ago a heparin-binding endothelial cell-growth factor called vascular endothelial growth factor (VEGF) was identified and purified from media conditioned by bovine pituitary follicular or folliculo-stellate cells. See Ferrara et al., *Biophys. Res. Comm.* 161, 851 (1989).

Although a vascular endothelial cell growth factor could be isolated and purified from natural sources for subsequent therapeutic use, the relatively low concentrations of the protein in FC and the high cost, both in terms of effort and expense, of recovering VEGF proved commercially unavailing. Accordingly, further efforts were undertaken to clone and express VEGF via recombinant DNA techniques. The embodiments of that research are set forth in the patent applications referred to supra; this research was also reported in the scientific literature in *Laboratory Investigation* 72, 615 (1995), and the references cited therein.

In those applications there is described an isolated nucleic acid sequence comprising a sequence that encodes a vascular endothelial cell growth factor having a molecular weight of about 45,000 daltons under non-reducing conditions and about 23,000 under reducing conditions as measured by SDS-PAGE. Both the DNA and amino acid sequences are set forth in figures forming a part of the present application— see infra.

VEGF prepared as described in the patent applications cited supra, is useful for treating conditions in which a selected action on the vascular endothelial cells, in the absence of excessive tissue growth, is important, for example, diabetic ulcers and vascular injuries resulting from trauma such as subcutaneous wounds. Being a vascular (artery and venus) endothelial cell growth factor, VEGF restores cells that are damaged, a process referred to as vasculogenesis, and stimulates the formulation of new vessels, a process referred to as angiogenesis.

VEGF is expressed in a variety of tissues as multiple homodimeric forms (121, 165, 189 and 206 amino acids per monomer) resulting from alternative RNA splicing. $VEGF_{121}$ is a soluble mitogen that does not bind heparin; the longer forms of VEGF bind heparin with progressively higher affinity. The heparin-binding forms of VEGF can be cleaved in the carboxy terminus by plasmin to release (a) diffusible form(s) of VEGF. Amino acid sequencing of the carboxy terminal peptide identified after plasmin cleavage is $Arg_{110}$–$Ala_{111}$. Amino terminal "core" protein, VEGF (1-110) isolated as a homodimer, binds neutralizing monoclonal antibodies (4.6.1 and 2E3) and soluble forms of FLT-1, KDR and FLK receptors with similar affinity compared to the intact $VEGF_{165}$ homodimer. VEGF contains a C-terminal heparin binding domain that generally spans the C-terminus beginning beyond about amino acid 120. Generally this domain carries a relatively large number of positively charged amino acids.

The present invention is predicated upon initial research results that compared the heparin binding properties of VEGF derived respectively from recombinant Chinese hamster ovary (CHO) and *E. coli* cells. This research resulted in the finding that the CHO-derived VEGF material contained various C-terminal "processing" resulting in forms having different lengths with respect to the heparin binding C-terminal domain versus the substantially full-length material derived via *E. coli* production. Such C-terminal processing includes internal clips, i.e., cleaved sites, within the heparin binding domain that may alter the secondary and tertiary structure of the heparin binding domain so as to decease its affinity for heparin and endogenous heparan sulfate proteoglycans.

Further research indicated that such C-terminal processing of VEGF resulted in variants exhibiting slower rates of clearance and smaller volumes of distribution. Although these processed variants still possess at least a portion of the heparin binding domain, the modified domain bound heparin and heparin sulfate proteoglycans with lower affinity. The resultant effect was that less VEGF was cleared by non-specific target organs such as the liver.

It was therefore a further object of this research to produce VEGF variants that would have C-terminal variations with consequential varying heparin binding affinity resulting in variants of VEGF having a reduced clearance rate and hence longer retention within the body after systemic administration such that lower doses of the material were available for systemic administration for therapeutic effect. The intellectual property of such research is the subject of the present invention.

SUMMARY OF THE INVENTION

The objects of this invention, as defined generally supra, are achieved by the provision of vascular endothelial cell growth factor (VEGF) variants having modifications in the C-terminus heparin binding domain, said variants exhibiting reduced clearance rates for systemic administration generally at lower doses compared with native VEGF thus providing variants having longer availability for therapeutic effect.

In a preferred embodiment, such modifications result in structural alterations effected within the region of the C-terminus heparin binding domain bridging about amino acid 121 to about amino acid 165, and more preferably around the protease sensitive sites at positions 125 and 147 and/or at other sites within the domain where structural alterations alter functional binding characteristics, such as at the loci of positively charged amino acids.

The variants hereof may be prepared via recombinant DNA technology taking advantage of the available tools and techniques for providing DNA having deletions in the C-terminal domain such that the recombinant expression of such DNA provides VEGF variants wherein the C-terminus heparin binding domain contain deletions with resultant altered pharmacological properties affecting therapeutic results. Alternatively, such variants can be isolated from recombinant systems that cause proteolytic cleavage at the C-terminus (a largely basic amino acid containing domain) resulting in C-terminus heparin binding domain deletion variants. Alternatively, such C-terminus deletion variants are products of for example carboxypeptidase B treatment.

In other aspects, the present invention relates to DNA sequences encoding the various variants described supra, replicable expression vectors capable of expressing said DNA sequences via transforming DNA in a transformant host cell, and microorganisms and cell cultures which are transformed with such vectors.

In further aspects hereof, the present invention is directed to methods useful for the recombinant expression of such DNA referred to above including methods of isolation and purification as a part of recovery.

In yet further aspects, the present invention is directed to compositions useful for treating indications where vasculogenesis or angiogenesis is desired for treatment of an underlying disease state comprising a therapeutically effective amount of a VEGF variant hereof, advantageously being reduced in general dosage form because of the reduced clearance rates exhibited by the variants hereof, in admixture with a pharmaceutically acceptable carrier. Thus, the present invention provides variants of VEGF wherein their exhibited reduced rate of clearance provides resultant effects that provide in turn safer alternative systemic administration with lower doses resulting in longer availability for therapeutic effect. In addition, a decrease in potential toxic side effects would be expected due to the decrease in nonspecific binding of the heparin domain modified variants to non-target tissues.

Thus, the present invention is directed to VEGF C-terminal heparin binding domain variants having structural alterations that result in functional modification of the heparin binding characteristics of that VEGF variant molecule. Such structural alterations can be imparted by, for example, internal cleavage at various proteolytic sites and/or by various mutations. For example structural alterations may change the ionic charge of the domain by replacement of the largely positively charged amino acids with negatively or neutrally charged amino acids and/or by other mutations resulting in derivatives such as by deletions of amino acids, substitutions, and so forth.

All such structural alterations are believed to result in molecules that have in turn altered conformational structure that affects the heparin binding characteristics. It is believed that because the heparin binding domain is a highly positively charged domain, the binding characteristics with heparin are probably an ionic interaction. Therefore, structural alterations that would affect ionic interaction would in turn affect binding. Thus, any such structural alterations that result in affecting heparin binding are covered within the scope of the present invention, i.e., such VEGF variants hereof manifest functional effect.

Expanding on the basic premise hereof based upon the finding of the effects of C-terminus heparin binding domain deletion variants of VEGF, the present invention is directed to all associated embodiments deriving therefrom, including recombinant DNA materials and processes for preparing such variants, materials and information for compounding such variants into pharmaceutically finished form and various assays using such variants.

BRIEF DESCRIPTION OF THE DRAWINGS

FIGS. 1A and 1B depict both the amino acid (SEQ ID NO:2) and DNA sequence (SEQ ID NO:1) for VEGF having 165 amino acids. Predicted amino acids of the protein are shown below the DNA sequence and are numbered from the first residue of the N-terminus of the protein sequence. Negative amino acid numbers refer to the presumed leader signal sequence or pre-protein, while positive numbers refer to the putative mature protein.

FIG. 2 depicts schematics of VEGF which include the C-terminus heparin binding domain of VEGF. The heparin binding domain is generally considered to be located from about amino acid 121 to the C-terminal amino acid of the full-length molecule (SEQ ID NO:3). The top panel of FIG. 2 shows a plasmin cleavage site and the bottom panel of FIG. 2 shows potential disulfide bonds between cysteine residues and clip sites at residues 110, 125 and 147.

FIG. 3 depicts the construction with its various elements of the plasmid pSDVF$_{165}$.

FIG. 4 depicts the construction with its various elements of the plasmid pRK5.

FIG. 5 depicts the construction schematic followed to prepare the final expression vectors harboring DNA that contains mutations in accordance with preparing the various products of the present invention.

FIG. 6 depicts the comparative pharmacokinetic (PK) study between *E. coli* and CHO VEGF in rats. It can be seen that the VEGF obtained from *E. coli* cleared more rapidly due to increased binding to heparin or endogenous heparin sulfate proteoglycans.

FIG. 7 depicts the calculated pharmacokinetic parameters for CHO versus *E. Coli* VEGF as given in FIG. 6 and FIG. 8, respectively.

FIG. 8 depicts [125I]—VEGF in isolated rat liver perfusion.

FIG. 9 depicts *E. coli* and CHO VEGF comparison by heparin column chromotography.

FIG. 10 depicts heparin chromatography of various VEGF samples.

FIG. 11 depicts the results of *E. coli*-derived VEGF after carboxypeptodase treatment compared with CHO-derived VEGF.

FIG. 12 depicts the CHO-derived VEGF peaks 1 and 2 by liver perfusion.

FIG. 13 displays the in vivo pharmacokinetics of *E. coli*-derived VEGF (control, peaks 1 and 2).

FIG. 14 displays the in vivo pharmacokinetics of *E. coli*-derived VEGF (control, peaks 1 and 2).

FIG. 16 shows the effect of VEGF variants on ACE cell proliferation.

FIGS. 17A–C depict data showing VEGF binding to red blood cells of various mammal species. FIG. 17A depicts results obtained from rat blood cells, FIG. 17B depicts results obtained from rabbit blood cells, and FIG. 17C depicts results obtained from human blood cells.

DETAILED DESCRIPTION OF THE INVENTION

A. Definitions

Figure 15:
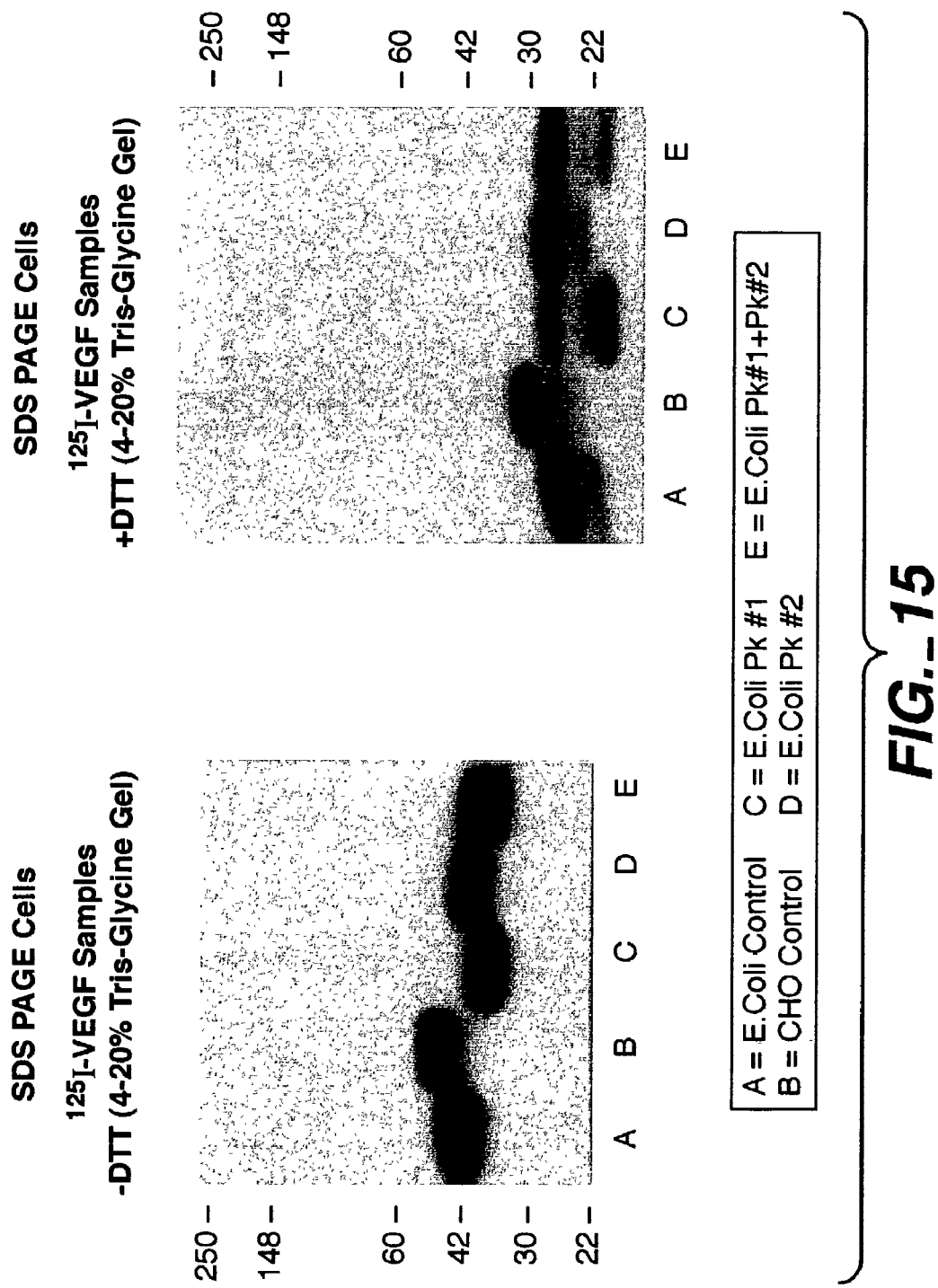
FIG. 15 depicts the SDS Page gel results of various iodinated VEGF samples.

As used herein, "vascular endothelial cell growth factor," or "VEGF," refers to a mammalian growth factor as defined in U.S. Pat. No. 5,332,671, including the human amino acid sequence of FIGS. 1A and 1B. The biological activity of native VEGF is shared by any analogue or variant thereof that is capable of promoting selective growth of vascular endothelial cells but not of bovine corneal endothelial cells, lens epithelial cells, adrenal cortex cells, BHK-21 fibroblasts, or keratinocytes, or that possesses an immune epitope that is immunologically cross-reactive with an antibody raised against at least one epitope of the corresponding native VEGF.

The term "variant" refers to VEGF molecules that contain a modification(s) in the C-terminus heparin binding domain that results in functional modification of the pharmacokinetic profile, that is, the production of a molecule having a reduced clearance rate compared with native material. It is believed that such modifications affect the confirmational structure of the resultant variant, hence the use of the term "structural alteration" in respect of such "modifications.". These modifications may be the result of DNA mutagenesis so as to create molecules having different amino acids from those found in the native material. In particular, as the C-terminus heparin binding domain contains a relatively large number of positively charged amino acids, the binding of that domain with heparin is believed to be based upon ionic interactions. Accordingly, preferred embodiments would replace positively charged amino acids with negatively or neutrally charged amino acids. Alternatively, the molecule may be modified by deleting portions of the C-terminal heparin binding domain. Still alternatively, proteolytic cleavage of the C-terminal heparin binding domain at various cleavage sites result in VEGF variants that have modifications resulting in reduced clearance rates. Thus, the present invention is directed to any modification to the C-terminal heparin binding domain of VEGF that results in a molecule that has affected pharmacokinetic properties i.e., a functional definition.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S.N. *Proc. Natl. Acad. Sci.* (USA), 69, 2110 (1972) and Mandel et al. *J. Mol. Biol.* 53, 154 (1970), is generally used for prokaryotes or other cells that contain substantial cell-wall barriers. For mammalian cells without such cell walls, the calcium phosphate precipitation method of Graham, F. and van der Eb, A., *Virology*, 52, 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al. *J. Bact.*, 130, 946 (1977) and Hsiao, C. L., et al. *Proc. Natl. Acad. Sci.* (USA) 76, 3829 (1979). However, other methods for introducing DNA into cells such as by nuclear injection or by protoplast fusion may also be used.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. The plaques are hybridized with kinased synthetic primer at a temperature that permits hybridization of an exact match, but at which the mismatches with the original strand are sufficient to prevent hybridization. Plaques that hybridize with the probe are then selected and cultured, and the DNA is recovered.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 mg of plasmid or DNA fragment is used with about 1–2 units of enzyme in about 20 ml of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al. 1982, *Molecular Cloning: A Laboratory Manual* (New York: Cold Spring Harbor Laboratory, 1982) pp.133–134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., *Nucleic Acids Res.* 9, 6103–6114 (1981), and D. Goeddel et al., *Nucleic Acids Res.* 8, 4057 (1980).

"Southern Analysis" is a method by which the presence of DNA sequences in a digest or DNA-containing composition is confirmed by hybridization to a known, labeled oligonucleotide or DNA fragment. For the purposes herein, unless otherwise provided, Southern analysis shall mean separation of digests on 1 percent agarose, denaturation, and transfer to nitrocellulose by the method of E. Southern, *J. Mol. Biol.* 98, 503–517 (1975), and hybridization as described by T. Maniatis et al., *Cell* 15, 687–701 (1978).

"Ligation" refers to the process of forming phosphodiester bonds between two double stranded nucleic acid fragments (T. Maniatis et al. 1982, supra, p.146). Unless otherwise provided, ligation may be accomplished using known buffers and conditions with 10 units of T4 DNA ligase ("ligase") per 0.5 mg of approximately equimolar amounts of the DNA fragments to be ligated.

"Preparation" of DNA from transformants means isolating plasmid DNA from microbial culture. Unless otherwise provided, the alkaline/SDS method of Maniatis et al. 1982, supra, p. 90, may be used.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP Pat. Pub. No. 266,032 published May 4, 1988, or via deoxynucleoside H-phosphonate intermediates as described by Froehler et al., *Nucl. Acids Res.* 14, 5399–5407[1986]). They are then purified on polyacrylamide gels.

B. General Methodology

1. Glycosylation

The VEGF amino acid sequence variant may contain at least one amino acid sequence that has the potential to be glycosylated through an N-linkage and that is not normally glycosylated in the native molecule.

2. Amino Acid Sequence Variants a. Additional Mutations

For purposes of shorthand designation of VEGF variants described herein, it is noted that numbers refer to the amino acid residue/position along the amino acid sequences of putative mature VEGF. Amino acid identification uses the single-letter alphabet of amino acids, i.e.,

| Asp | D | Aspartic acid | Ile | I | Isoleucine |
|-----|---|---------------|-----|---|------------|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

The present invention is directed to C-terminus heparin binding domain variants of VEGF. These variants forming the predicate of the present invention may also contain additional variations within the backbone of the VEGF molecule which does not affect the biological properties of the VEGF fundamental variant hereof in kind.

It will be appreciated that those certain other variants at other positions in the VEGF molecule can be made without departing from the spirit of the present invention with respect to the C-terminus heparin binding domain deletion variations hereof. Thus, point mutational or other broader variations may be made in all other parts of the molecule so as to impart interesting properties that again do not affect the overall properties of the fundamental variant with respect to the C-terminal deletion. These latter, additional variants may be made by means generally known in the art. For example covalent modifications may be made to various of the amino acid residues.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, a-bromo-b-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $_{125}I$ or $_{131}I$ to prepare labeled proteins for use in radioimmunoassay, the chloramine T method described above being suitable.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the VEGF to a water-insoluble support matrix or surface for use in the method for purifying anti-VEGF antibodies. Commonly used crosslinking agents include, e.g., 1,1-bis(diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, Proteins: *Structure and Molecular Properties*, W. H. Freeman & Co., San Francisco, pp. 79–86[1983]), acetylation of the N-terminal amine, and, in some instances, amidation of the C-terminal carboxyl group.

b. DNA Mutations

Amino acid sequence variants of VEGF can also be prepared by mutations in the DNA. Such variants include, for example, deletions from, or insertions or substitutions of, residues within the amino acid sequence shown in FIGS. 1A and 1B. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP 75,444A).

At the genetic level, these variants ordinarily are prepared by site-directed mutagenesis of nucleotides in the DNA encoding the VEGF, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed VEGF variants screened for the optimal combination of desired activity. Techniques for making substitution mutations at predetermined sites in DNA having a known sequence are well known, for example, site-specific mutagenesis.

Preparation of VEGF variants in accordance herewith is preferably achieved by site-specific mutagenesis of DNA that encodes an earlier prepared variant or a nonvariant version of the protein. Site-specific mutagenesis allows the production of VEGF variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2, 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.*, 153, 3[1987]) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (USA), 75, 5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

c. Types of Mutations

Amino acid sequence deletions generally range from about 1 to 30 residues, more preferably 1 to 10 residues, and typically are contiguous.

Amino acid sequence insertions include amino- and/or carboxyl-terminal fusions of from one residue to polypeptides of essentially unrestricted length, as well as intrasequence insertions of single or multiple amino acid residues. Intrasequence insertions (i.e., insertions within the mature VEGF sequence) may range generally from about 1 to 10 residues, more preferably 1 to 5. An example of a terminal insertion includes a fusion of a signal sequence, whether heterologous or homologous to the host cell, to the N-terminus of the VEGF molecule to facilitate the secretion of mature VEGF from recombinant hosts.

The third group of variants are those in which at least one amino acid residue in the VEGF molecule, and preferably only one, has been removed and a different residue inserted in its place. Such substitutions preferably are made in accordance with the following Table 1 when it is desired to modulate finely the characteristics of a VEGF molecule.

TABLE 1

| Original Residue | Exemplary Substitutions |
|---|---|
| Ala (A) | gly; ser |
| Arg (R) | lys |
| Asn (N) | gln; his |
| Asp (D) | glu |
| Cys (C) | ser |
| Gln (Q) | asn |
| Glu (E) | asp |
| Gly (G) | ala; pro |
| His (H) | asn; gln |
| Ile (I) | leu; val |
| Leu (L) | ile; val |
| Lys (K) | arg; gln; glu |
| Met (M) | leu; tyr; ile |
| Phe (F) | met; leu; tyr |
| Ser (S) | thr |
| Thr (T) | ser |
| Trp (W) | tyr |
| Tyr (Y) | trp; phe |
| Val (V) | ile; leu |

Substantial changes in function or immunological identity are made by selecting substitutions that are less conservative than those in Table I, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in VEGF properties will be those in which (a) glycine and/or proline (P) is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; (e) a residue having an electronegative side chain is substituted for (or by) a residue having an electropositive charge; or (f) a residue having a bulky side chain, e.g., phenylalanine, is substituted for (or by) one not having such a side chain, e.g., glycine.

Most deletions and insertions, and substitutions in particular, are not expected to produce radical changes in the characteristics of the VEGF molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native VEGF-encoding nucleic acid, expression of the variant nucleic acid in recombinant cell culture, and, optionally, purification from the cell culture, for example, by immunoaffinity adsorption on a rabbit polyclonal anti-VEGF column (to absorb the variant by binding it to at least one remaining immune epitope).

Since VEGF tends to aggregate into dimers, it is within the scope hereof to provide hetero- and homodimers, wherein one or both subunits are variants. Where both subunits are variants, the changes in amino acid sequence can be the same or different for each subunit chain. Heterodimers are readily produced by cotransforming host cells with DNA encoding both subunits and, if necessary, purifying the desired heterodimer, or by separately synthesizing the subunits, dissociating the subunits (e.g., by treatment with a chaotropic agent such as urea, guanidine hydrochloride, or the like), mixing the dissociated subunits, and then reassociating the subunits by dialyzing away the chaotropic agent.

Also included within the scope of mutants herein are so-called glyco-scan mutants. This embodiment takes advantage of the knowledge of so-called glycosylation sites. Thus, where appropriate such a glycosylation site can be introduced so as to produce a species containing glycosylation moieties at that position. Similarly, an existing glycosylation site can be removed by mutation so as to produce a species that is devoid of glycosylation at that site. It will be understood, again, as with the other mutations contemplated by the present invention, that they are introduced within the so-called KDR and/or FLT-1 domains in accord with the basic premise of the present invention, and they can be introduced at other locations outside of these domains within the overall molecule so long as the final product does not differ in overall kind from the properties of the mutation introduced in one or both of said two binding domains.

The activity of the cell lysate or purified VEGF variant is then screened in a suitable screening assay for the desired characteristic. For example, a change in the immunological character of the VEGF molecule, such as affinity for a given antibody, is measured by a competitive-type immunoassay. Changes in the enhancement or suppression of vascular endothelium growth by the candidate mutants are measured by the appropriate assay. Modifications of such protein properties as redox or thermal stability, hydrophobicity, susceptibility to proteolytic degradation, or the tendency to aggregate with carriers or into multimers are assayed by methods well known to the ordinarily skilled artisan.

3. Recombinant Expression

The VEGF molecule desired may be prepared by any technique, including recombinant methods. Likewise, an isolated DNA is understood herein to mean chemically synthesized DNA, cDNA, chromosomal, or extrachromosomal DNA with or without the 3'- and/or 5'-flanking regions. Preferably, the desired VEGF herein is made by synthesis in recombinant cell culture.

For such synthesis, it is first necessary to secure nucleic acid that encodes a VEGF. DNA encoding a VEGF molecule may be obtained from bovine, pituitary follicular cells by (a) preparing a cDNA library from these cells, (b) conducting hybridization analysis with labeled DNA encoding the VEGF or fragments thereof (up to or more than 100 base pairs in length) to detect clones in the library containing homologous sequences, and (c) analyzing the clones by restriction enzyme analysis and nucleic acid sequencing to identify full-length clones. DNA that is capable of hybridizing to a VEGF-encoding DNA under low stringency conditions is useful for identifying DNA encoding VEGF. Both high and low stringency conditions are defined further below. If full-length clones are not present in a cDNA library, then appropriate fragments may be recovered from the various clones using the nucleic acid sequence information disclosed herein for the first time and ligated at restriction sites common to the clones to assemble a full-length clone encoding the VEGF. Alternatively, genomic libraries will provide the desired DNA. The sequence of the DNA encoding human VEGF that was ultimately determined by probing a human leukemia cell line is shown in FIGS. 1A and 1B.

Once this DNA has been identified and isolated from the library it is ligated into a replicable vector for further cloning or for expression.

In one example of a recombinant expression system a VEGF-encoding gene is expressed in mammalian cells by transformation with an expression vector comprising DNA encoding the VEGF. It is preferable to transform host cells capable of accomplishing such processing so as to obtain the VEGF in the culture medium or periplasm of the host cell, i.e., obtain a secreted molecule.

a. Useful Host Cells and Vectors

The vectors and methods disclosed herein are suitable for use in host cells over a wide range of prokaryotic and eukaryotic organisms.

In general, of course, prokaryotes are preferred for the initial cloning of DNA sequences and construction of the vectors useful in the invention. For example, *E coli* K12 strain MM 294 (ATCC No. 31,446) is particularly useful. Other microbial strains that may be used include *E. coli* strains such as *E. coli* B and *E. coli* X 1776 (ATCC No. 31,537). These examples are, of course, intended to be illustrative rather than limiting.

Prokaryotes may also be used for expression. The aforementioned strains, as well as *E. coli* strains W3110 (F-, lambda-, prototrophic, ATCC No. 27,325), K5772 (ATCC No. 53,635), and SR101*, bacilli* such as *Bacillus subtilis*, and other enterobacteriaceae such as *Salmonella typhimurium* or *Serratia marcesans*, and various pseudomonas species, may be used.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene* 2, 95[1977]). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the b-lactamase (penicillinase) and lactose promoter systems (Chang et al., *Nature,* 375, 615[1978]; Itakura et al., *Science,* 198, 1056[1977]; Goeddel et al., *Nature,* 281, 544[1979]) and a tryptophan (trp) promoter system (Goeddel et al., *Nucleic Acids Res.,* 8, 4057 [1980]; EPO Appl. Publ. No. 0036,776). While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell,* 20, 269[1980]).

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in *Saccharomyces*, the plasmid YRp7, for example (Stinchcomb et al., *Nature* 282, 39[1979]; Kingsman et al., *Gene* 7,141[1979]; Tschemper et al., *Gene* 10, 157[1980]), is commonly used. This plasmid already contains the trp1 gene that provides a selection marker for a mutant strain of yeast lacking the ability to grow in tryptophan, for example, ATCC No. 44,076 or PEP4-1 (Jones, *Genetics,* 85, 12[1977]). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.* 255, 2073[1980]) or other glycolytic enzymes (Hess et al., *J. Adv. Enzyme Reg.* 7,149[1968]; Holland et al., *Biochemistry* 17, 4900[1978]), such as enolase, glyceraldehyde-3-phosphate dehydrogenase, hexokinase, pyruvate decarboxylase, phosphofructo-kinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication [Fiers et al., *Nature*, 273, 113 (1978)]. Smaller or larger SV40 fragments may also be used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell for transfection by the vectors of the invention that comprise DNA sequences encoding both VEGF and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci. (USA)* 77, 4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

b. Typical Methodology Employable

Construction of suitable vectors containing the desired coding and control sequences employs standard ligation techniques. Isolated plasmids or DNA fragments are cleaved, tailored, and religated in the form desired to prepare the plasmids required.

If blunt ends are required, the preparation may be treated for 15 minutes at 15° C. with 10 units of Polymerase I (Klenow), phenol-chloroform extracted, and ethanol precipitated.

Size separation of the cleaved fragments may be performed using 6 percent polyacrylamide gel described by Goeddel et al., *Nucleic Acids Res.* 8, 4057 (1980).

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.* 9, 309 (1981) or by the method of Maxam et al., *Methods of Enzymology* 65, 499 (1980).

After introduction of the DNA into the mammalian cell host and selection in medium for stable transfectants, amplification of DHFR-protein-coding sequences is effected by growing host cell cultures in the presence of approximately 20,000–500,000 nM concentrations of methotrexate, a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

Other techniques employable are described in a section just prior to the examples.

4. Utilities and Formulation

The VEGF molecules herein have a number of therapeutic uses associated with the vascular endothelium. Such uses include the treatment of traumata to the vascular network, in view of the demonstrated rapid promotion by VEGF of the proliferation of vascular endothelial cells that would surround the traumata. Examples of such traumata that could be so treated include, but are not limited to, surgical incisions, particularly those involving the heart, wounds, including lacerations, incisions, and penetrations of blood vessels, and surface ulcers involving the vascular endothelium such as diabetic, hemophiliac, and varicose ulcers. Other physiological conditions that could be improved based on the selective mitogenic character of VEGF are also included herein.

For the traumatic indications referred to above, the VEGF molecule will be formulated and dosed in a fashion consistent with good medical practice taking into account the specific disorder to be treated, the condition of the individual patient, the site of delivery of the VEGF, the method of administration, and other factors known to practitioners. Thus, for purposes herein, the "therapeutically effective amount" of the VEGF is an amount that is effective either to prevent, lessen the worsening of, alleviate, or cure the treated condition, in particular that amount which is sufficient to enhance the growth of vascular endothelium in vivo.

VEGF amino acid sequence variants and derivatives that are immunologically crossreactive with antibodies raised against native VEGF are useful in immunoassays for VEGF as standards, or, when labeled, as competitive reagents.

The VEGF is prepared for storage or administration by mixing VEGF having the desired degree of purity with physiologically acceptable carriers, excipients, or stabilizers. Such materials are non-toxic to recipients at the dosages and concentrations employed. If the VEGF is water soluble, it may be formulated in a buffer such as phosphate or other organic acid salt preferably at a pH of about 7 to 8. If a VEGF variant is only partially soluble in water, it may be prepared as a microemulsion by formulating it with a nonionic surfactant such as Tween, Pluronics, or PEG, e.g., Tween 80, in an amount of 0.04–0.05% (w/v), to increase its solubility.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

The VEGF to be used for therapeutic administration must be sterile. Sterility is readily accomplished by filtration through sterile filtration membranes (e.g., 0.2 micron membranes). The VEGF ordinarily will be stored in lyophilized form or as an aqueous solution if it is highly stable to thermal and oxidative denaturation. The pH of the VEGF preparations typically will be about from 6 to 8, although higher or lower pH values may also be appropriate in certain instances. It will be understood that use of certain of the foregoing excipients, carriers, or stabilizers will result in the formation of salts of the VEGF.

If the VEGF is to be used parenterally, therapeutic compositions containing the VEGF generally are placed into a container having a sterile access port, for example, an intravenous solution bag or vial having a stopper pierceable by a hypodermic injection needle.

Generally, where the disorder permits, one should formulate and dose the VEGF for site-specific delivery. This is convenient in the case of wounds and ulcers.

Sustained release formulations may also be prepared, and include the formation of microcapsular particles and implantable articles. For preparing sustained-release VEGF compositions, the VEGF is preferably incorporated into a biodegradable matrix or microcapsule. A suitable material for this purpose is a polylactide, although other polymers of poly-(a-hydroxycarboxylic acids), such as poly-D-(-)-3-hydroxybutyric acid (EP 133,988A), can be used. Other biodegradable polymers include poly(lactones), poly(acetals), poly(orthoesters), or poly(orthocarbonates). The initial consideration here must be that the carrier itself, or its degradation products, is nontoxic in the target tissue and will not further aggravate the condition. This can be determined by routine screening in animal models of the target disorder or, if such models are unavailable, in normal animals. Numerous scientific publications document such animal models.

For examples of sustained release compositions, see U.S. Pat. No. 3,773,919, EP 58,481A, U.S. Pat. No. 3,887,699, EP 1 58,277A, Canadian Patent No. 1176565, U. Sidman et al., *Biopolymers* 22, 547[1983], and R. Langer et al., *Chem. Tech.* 12, 98[1982].

When applied topically, the VEGF is suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the VEGF formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the VEGF held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2–5%, more preferably about 3%, of the gel and the VEGF is present in an amount of about 300–1000 mg per ml of gel.

The dosage to be employed is dependent upon the factors described above. As a general proposition, the VEGF is formulated and delivered to the target site or tissue at a dosage capable of establishing in the tissue a VEGF level greater than about 0.1 ng/cc up to a maximum dose that is efficacious but not unduly toxic. This intra-tissue concentration should be maintained if possible by continuous infusion, sustained release, topical application, or injection at empirically determined frequencies.

It is within the scope hereof to combine the VEGF therapy with other novel or conventional therapies (e.g., growth factors such as aFGF, bFGF, PDGF, IGF, NGF, anabolic steroids, EGF or TGF-a) for enhancing the activity of any of the growth factors, including VEGF, in promoting cell proliferation and repair. It is not necessary that such cotreatment drugs be included per se in the compositions of this invention, although this will be convenient where such drugs are proteinaceous. Such admixtures are suitably administered in the same manner and for the same purposes as the VEGF used alone. The useful molar ratio of VEGF to such secondary growth factors is typically 1:0.1–10, with about equimolar amounts being preferred.

5. Pharmaceutical Compositions

The compounds of the present invention can be formulated according to known methods to prepare pharmaceutically useful compositions, whereby the VEGF variants hereof is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences*, 16th ed., 1980, Mack Publishing Co., edited by Oslo et al. the disclosure of which is hereby incorporated by reference. The VEGF variants herein may be administered parenterally to subjects suffering from cardiovascular diseases or conditions, or by other methods that ensure its delivery to the bloodstream in an effective form.

Compositions particularly well suited for the clinical administration of VEGF variants hereof employed in the practice of the present invention include, for example, sterile aqueous solutions, or sterile hydratable powders such as lyophilized protein. It is generally desirable to include further in the formulation an appropriate amount of a pharmaceutically acceptable salt, generally in an amount sufficient to render the formulation isotonic. A pH regulator such as arginine base, and phosphoric acid, are also typically included in sufficient quantities to maintain an appropriate pH, generally from 5.5 to 7.5. Moreover, for improvement of shelf-life or stability of aqueous formulations, it may also be desirable to include further agents such as glycerol. In this manner, variant t-PA formulations are rendered appropriate for parenteral administration, and, in particular, intravenous administration.

Dosages and desired drug concentrations of pharmaceutical compositions of the present invention may vary depending on the particular use envisioned. For example, in the treatment of deep vein thrombosis or peripheral vascular disease, "bolus" doses, will typically be preferred with subsequent administrations being given to maintain an approximately constant blood level, preferably on the order of about 3 μg/ml.

However, for use in connection with emergency medical care facilities where infusion capability is generally not available and due to the generally critical nature of the underlying disease (e.g., embolism, infarct), it will generally be desirable to provide somewhat larger initial doses, such as an intravenous bolus.

For the various therapeutic indications referred to for the compounds hereof, the VEGF molecules will be formulated and dosed in a fashion consistent with good medical practice taking into account the specific disorder to be treated, the condition of the individual patient, the site of delivery, the method of administration and other factors known to practitioners in the respective art. Thus, for purposes herein, the "therapeutically effective amount" of the VEGF molecules hereof is an amount that is effective either to prevent, lessen the worsening of, alleviate, or cure the treated condition, in particular that amount which is sufficient to enhance the growth of vascular endothelium in vivo. In general a dosage is employed capable of establishing in the tissue that is the target for the therapeutic indication being treated a level of a VEGF mutant hereof greater than about 0.1 ng/cm$^3$ up to a maximum dose that is efficacious but not unduly toxic. It is contemplated that intra-tissue administration may be the choice for certain of the therapeutic indications for the compounds hereof.

The following examples are intended merely to illustrate the best mode now known for practicing the invention but the invention is not to be considered as limited to the details of such examples.

EXAMPLES

Vascular Endothelial Growth Factor (VEGF) is a heparin binding growth factor that may be clinically beneficial for revascularization of ischemic tissues. Significant differences in the pharmacological profile of Chinese hamster ovary (CHO) and *E. coli*-derived VEGF have been observed. The purpose of this study was to determine the molecular basis for the pharmacologic differences between CHO and *E. coli* VEGF. Isolated rat liver perfusion and whole animal pharmacokinetic studies were used in conjunction with heparin column chromatography and mass spectral analysis to characterize differences in clearance determinants. *E. coli* VEGF had a greater first pass hepatic extraction and higher volume of distribution when compared with CHO VEGF.

|  | *E. coli* VEGF | CHO VEGF |
|---|---|---|
| CL (mL/min/kg) | 11.5 | 4.0 |
| Vdss (mL/kg) | 1358.6 | 1263.9 |

Preincubation of *E. coli* VEGF with heparin reduced hepatic extraction suggesting that heparin sulfate proteoglycan binding was in part responsible for the rapid hepatic uptake. Using heparin column chromatography, differences in the binding affinity between CHO and *E. coli* VEGF were noted. CHO VEGF appeared heterogeneous and eluted earlier. Mass spectral analysis of the reduced and carboxy methylated CHO VEGF revealed internal proteolytic clips within the C-terminal heparin binding domain. *E. coli* VEGF behaved similarly to CHO VEGF in vitro and in vivo following limited proteolysis. These results demonstrate that the CHO VEGF was proteolytically clipped in the C-terminal heparin binding region which gave rise to reduced heparin binding and hence, a slower clearance and lower volumn of distribution in vivo.

Comparison of the heparin binding properties of CHO and *E. coli* derived VEGF: Three lots of CHO and two lots of *E. coli*-derived VEGF were analyzed using heparin column (Pharmacia) chromatography. Linear NaCl gradients (150 mM to 2.0 M NaCl, 10 mM NaP pH 7.4, 0.01% T-20) were used at a 0.5–1 ml/min flow rate for elution. The CHO lots appeared to be heterogeneous when compared to the VEGF produced in *E. coli*. CHO derived VEGF appeared as a doublet with approximately 40% total peak area eluting at 520 mM NaCl (peak 1) and 60% of the total peak area eluting at approximately 720 mM NaCl (peak 2). Additional peaks co-eluting with peak 1 were apparent when shallower gradients were used. In contrast, the *E. coli* derived VEGF appeared as a single homogeneous peak following heparin column chromatography under identical conditions. The *E. coli* VEGF had a slightly longer retention time, requiring approximately 745 mM NaCl for elution.

Heparin binding differences are not related to sialic acid content: Studies were done to investigate the possibility that glycosylation heterogeneity gave rise to the multiple peaks observed in the chromatograms of CHO-VEGF following heparin chromatography. In the first study CHO VEGF was treated with neurominadase to remove sialic acid. Quantitative removal of sialic acid was verified by Dionex (L. Basa). The retention time of CHO VEGF on heparin was unchanged following sialic acid removal, suggesting that differences in peak 1 and peak 2 was not due to differences in sialic acid content.

In the second study, peaks 1 and 2 were collected separately and compared to unfractionated CHO by isoelectric focusing. Acidic bands were represented in all peaks, however, there was a notable absence of more basic bands in the earlier eluting peak 1. These data provided further evidence that the multiple peaks observed following heparin column chromatography were not due to differences in sialic acid content. Instead, it appeared that peak 1 was lacking basic bands, rather than having additional acidic bands, when compared to peak 2. The C-terminal region of VEGF is highly basic and known to be important for heparin binding, thus it was reasoned that the apparent heterogeneity in the heparin binding affinity of VEGF could be due to C-terminal removal of basic amino acids within the heparin binding domain.

C-terminal degradation of CHO VEGF: Peak 1 and peak 2 eluting from heparin were collected separately following heparin column chromatography and were analyzed by SDS-PAGE and LC-MS. For SDS-PAGE analysis, the different fractions were radioiodinated to enhance the sensitivity of detection of various molecular forms of VEGF. Peak 1 and peak 2 were run under reducing and non-reducing conditions. Both peaks appeared to be similar to a control under non-reducing conditions and all fractions ran at the expected molecular weight (43 kDA). However, heterogeneity was apparent under reducing conditions. Multiple bands ranging in molecular weight from 15 to 20 kDA were apparent in the peak 1 fraction, whereas peak 2 only had 1 minor band lower than the expected molecular weight of VEGF monomer.

Mass spec analysis of the N-glyconase, reduced and carboxymethylated VEGF indicated that peak 2, the major peak represented VEGF 163/163. Peak 1 represented VEGF that had been further clipped within disulfied bonds C-terminal to amino acids 110, 125, and 147. These data indicate that the apparent heterogeneity in the CHO VEGF are a result of C-terminal processing with the heparin binding domain. Lastly, limited digestion of *E. coli* VEGF with carboxypeptidase B resulted in a peak that co-eluted with CHO peak 2. Mass spec analysis of this peak revealed that this peak was VEGF 163/163. A peak with similar retention time to peak 1 was observed following prolonged treatment (24 h) with carboxypeptidase B. Thus *E. coli* VEGF can be made to "behave" like CHO VEGF with respect to heparin binding following limited C-terminal digestion with CPB.

One milligram aliquots (200 µl) of rhVEGF$_{165}$ lot D9837A were diluted to 1 mL with 0.2 M NH$_4$HCO$_3$. Worthington PMSF treated CpB was added to the rhVEGF$_{165}$ solutions at an enzyme:substrate ratio of 1:50. The samples were digested at ambient temperature for 18 hours. The CpB digested rhVEGF$_{165}$ samples were purified by heparin chromatography. The preparatively collected fractions were pooled, then concentrated, using a Amicon Centricon-10 concentrator. The concentrated fractions were reformulated into 5 mM succinate, 275 mM trehalose by a Centricon-10 concentrator. After the fractions were concentrated, 0.1% Tween-20 was added to the solutions. Protein concentration of each fraction was determined by heparin chromatography and compared to peak areas of a standard solution of rhVEGF$_{165}$ D9837A.

Heparin Chromatographic Conditions:
Column: TosoHass Heparin-5PW column 7.5 mm×7.5 cm
Flow rate: 1.0 mL/minute
Detection: UV absorbance at 214 nm
Mobile phase:
    A: 10 mM NaH$_2$PO$_4$, 150 mM NaCl, pH 7.4
    B: 10 mM NaH$_2$PO$_4$, 2 M NaCl, pH 7.4
Gradient: 0% B to 80% B in 30 minutes linear Large Scale Experiments:
Large scale experiments were performed on batched of 4 vial. Four vials of M3RD587 were concentrated and reformulated in 0.2 m NH$_4$HCO$_3$ to approximately 1.5 mL (7.7 mg/mL) using a Centricon-10 concentrator. Worthington PMSF treated CpB was added to the rhVEGF$_{165}$ solutions at an enzyme:substrate ratio of 1:50. The samples were digested at 37° C. for 30 to 40 minutes. The CpB digested rhVEGF$_{165}$ samples were purified by heparin chromatography. The preparatively collected fractions were pooled, then concentrated using a Amicon Centriprep-10 concentrator. The concentrated fractions were reformulated into 5 mM succinate, 275 mM trehalose using the same Centriprep-10 concentrator. After the fractions were concentrated, 0.1% Tween-20 was added to the solutions. Protein concentration was determined by absorbance at 276 nm and amino acid analysis.

Heparin Chromatographic conditions:
Column: Pharmacia 5 mL HiTrap Heparin column
Flow rate: 2.0 mL/minute
Detection: UV absorbance at 214 nm
Mobile phase:
    A: 10 mM NaH$_2$PO$_4$, 150 mM NaCl, pH 7.4
    B: 10 mM NaH$_2$PO$_4$, 2 M NaCl, pH 7.4
Gradient: 0% B to 80% B in 30 minutes linear Effect of VEGF variants on ACE cell proliferation: Bovine adrenal cortical endothelial (ACE) cells were plated on 6-well plates at 6000 cells/well and cultured in medium containing 10% fetal calf serum. VEGF was added to the medium on the first day of culture at a concentration of 1 nM. ACE cells were trypsinized on day 5 and counted in a Casy-1 cell counter. Control cultures received diluting buffer in place of VEGF. Data represent a mean of 5 replicate samples (n=5). These data indicate that VEGF modified in the heparin binding domain still retain biological activity (i.e., the ability to stimulate endothelial cells to grow in culture).

Effect of heparin on VEGF binding to blood cells in rats and rabbits: The attached figure demonstrates that radioiodinated *E. coli* VEGF binds to blood cells in rabbits and rats to a greater extent that CHO VEGF. Modifying the *E. coli*-derived VEGF by limited proteolysis (see EC1+2) decrease this interaction. The fact that the 110/110 form of VEGF does not associate with the blood cell pellet provides further evidence that VEGF binding to RBCs appears is mediated by the heparin binding domain. These data further demonstrate that modification of the heparin binding domain could limit the loss of rhVEGF to nonspecific binding on various tissues (in this case the example being blood cells).

Concluding Remarks

The foregoing description details specific methods which can be employed to practice the present invention. Having detailed such specific methods, those skilled in the art will well enough know how to devise alternative reliable methods at arriving at the same information in using the fruits of the present invention. Thus, however detailed the foregoing may appear in text, it should not be construed as limiting the overall scope thereof; rather, the ambit of the present invention is to be determined only by the lawful construction of the appended claims. All documents cited herein are hereby expressly incorporated by reference.

We claim:

1. A pharmaceutical composition comprising a vascular endothelial cell growth factor (VEGF) variant polypeptide and a pharmaceutically acceptable carrier, wherein said variant polypeptide differs from native VEGF comprising a C-terminal heparin binding domain by comprising a structural alteration of the C-terminal heparin binding domain resulting in modified pharmacokinetic properties of said variant as compared to native VEGF, wherein said variant binds heparin at a lower affinity than said native VEGF, and wherein said structural alteration is a truncation of said heparin binding domain.

2. A pharmaceutical composition comprising a vascular endothelial cell growth factor (VEGF) variant polypeptide and a pharmaceutically acceptable carrier wherein said variant polypeptide differs from native VEGF by containing a C-terminal heparin binding domain structural alteration such that said domain binds heparin at a lower affinity than native VEGF comprising a heparin binding domain, resulting in said VEGF variant polypeptide having a reduced clearance rate compared with native VEGF, and wherein said structural alteration is a truncation of said heparin binding domain.

3. The composition according to claim 1 or 2, wherein said truncation comprises a reduction in positively charged amino acids.

4. The composition according to claim 3, wherein said C-terminal heparin binding domain of said VEGF variant polypeptide has an altered conformational structure as compared to said native VEGF.

5. The composition according to claim 1 or 2, wherein said C-terminal heparin binding domain is truncated at about amino acid 120.

6. The composition according to claim 1 or 2, wherein said C-terminal heparin binding domain is truncated at about amino acid 125.

7. The composition according to claim 1 or 2, wherein said C-terminal heparin binding domain is truncated at about amino acid 147.

* * * * *

UNITED STATES PATENT AND TRADEMARK OFFICE
CERTIFICATE OF CORRECTION

PATENT NO. : 7,208,472 B2  Page 1 of 1
APPLICATION NO. : 10/200050
DATED : April 24, 2007
INVENTOR(S) : Zioncheck et al.

It is certified that error appears in the above-identified patent and that said Letters Patent is hereby corrected as shown below:

Title page, (57) Abstract, line 3: "having modifications in the" should read --having structural alterations in the--

Title page, (57) Abstract, line 4: "domain. The variants" should read --domain and methods of use. The variants--

Col. 1, line 20: "17 Oct. 1996; and" should read --17 Oct. 1996, now U.S. Pat. No. 6,750,044; and--

Col. 23, line 12: "(in this case the example being blood cells)." should read --in this case the example being blood cells) when VEGF is coadministered with heparin.--

Signed and Sealed this

Fifteenth Day of April, 2008

JON W. DUDAS
*Director of the United States Patent and Trademark Office*